US010694977B2

(12) United States Patent
Forsell

(10) Patent No.: US 10,694,977 B2
(45) Date of Patent: *Jun. 30, 2020

(54) DEVICE FOR TREATMENT OF ANEURYSM

(71) Applicant: Peter Forsell, Bouveret (CH)

(72) Inventor: Peter Forsell, Bouveret (CH)

( * ) Notice: Subject to any disclaimer, the term of this patent is extended or adjusted under 35 U.S.C. 154(b) by 120 days.

This patent is subject to a terminal disclaimer.

(21) Appl. No.: 15/790,134

(22) Filed: Oct. 23, 2017

(65) Prior Publication Data

US 2018/0103872 A1 Apr. 19, 2018

Related U.S. Application Data

(63) Continuation of application No. 12/682,501, filed as application No. PCT/SE2008/000558 on Oct. 10, 2008, now Pat. No. 9,795,320.

(Continued)

(51) Int. Cl.
*A61B 5/07* (2006.01)
*A61B 5/02* (2006.01)
*A61B 5/00* (2006.01)
*A61B 17/12* (2006.01)
*A61B 17/135* (2006.01)
*A61M 1/12* (2006.01)
*A61M 1/10* (2006.01)

(Continued)

(52) U.S. Cl.
CPC .......... *A61B 5/076* (2013.01); *A61B 5/02007* (2013.01); *A61B 5/4393* (2013.01); *A61B 5/6862* (2013.01); *A61B 5/6876* (2013.01); *A61B 5/6885* (2013.01); *A61B 17/12009* (2013.01); *A61B 17/1355* (2013.01); *A61B 2017/00221* (2013.01); *A61B 2017/00411* (2013.01); *A61B 2017/00703* (2013.01); *A61B 2017/00734* (2013.01); *A61B 2090/065* (2016.02); *A61B 2562/0247* (2013.01); *A61B 2562/0261* (2013.01); *A61F 2002/3067* (2013.01); *A61F 2002/30668* (2013.01); *A61F 2250/0001* (2013.01); *A61F 2250/0002* (2013.01); *A61M 1/10* (2013.01); *A61M 1/107* (2013.01); *A61M 1/12* (2013.01); *A61M 1/125* (2014.02)

(58) Field of Classification Search
CPC .......... A61M 1/10; A61M 1/12; A61M 1/125; A61M 1/107
See application file for complete search history.

(56) References Cited

U.S. PATENT DOCUMENTS 6,030,336 A * 2/2000 Franchi ................. A61M 1/106
600/16
6,050,932 A * 4/2000 Franchi ............... A61M 1/1072
600/16

(Continued)

FOREIGN PATENT DOCUMENTS

WO WO-9919010 A1 * 4/1999 .......... A61M 1/3621

*Primary Examiner* — Diane D Yabut

(57) ABSTRACT

A device for treating a vascular aneurysm of a human or mammal patient, comprising an implantable member adapted to hold fluid, the implantable member being adapted to be placed against an outside of a blood vessel having the aneurysm, exercise a pressure on the aneurysm to prevent or reduce an expansion of the aneurysm, follow an outer contour of the aneurysm, and provide a pressure that is equal or less than the diastolic blood pressure of the human or mammal patient.

19 Claims, 16 Drawing Sheets

Related U.S. Application Data

(60) Provisional application No. 60/960,715, filed on Oct. 11, 2007, provisional application No. 60/960,716, filed on Oct. 11, 2007.

(51) Int. Cl.
*A61B 17/00* (2006.01)
*A61F 2/30* (2006.01)
*A61B 90/00* (2016.01)

(56) References Cited

U.S. PATENT DOCUMENTS

2003/0233023 A1* 12/2003 Khaghani ............ A61M 1/107
                                                                600/18
2007/0100368 A1*  5/2007 Quijano ............... A61F 5/0036
                                                                606/192

* cited by examiner

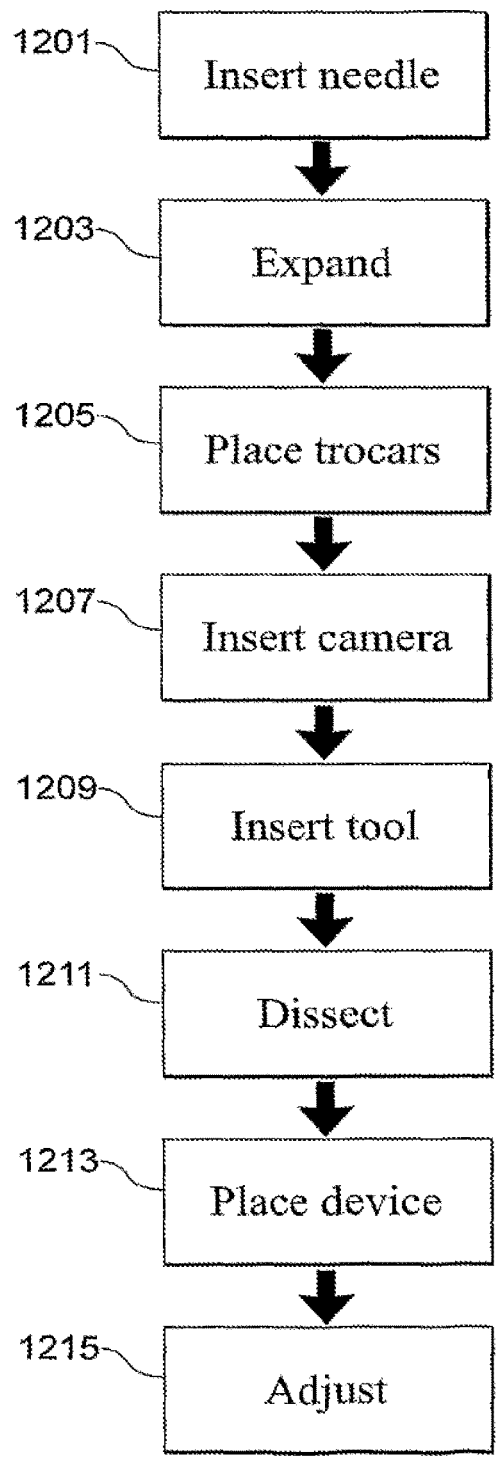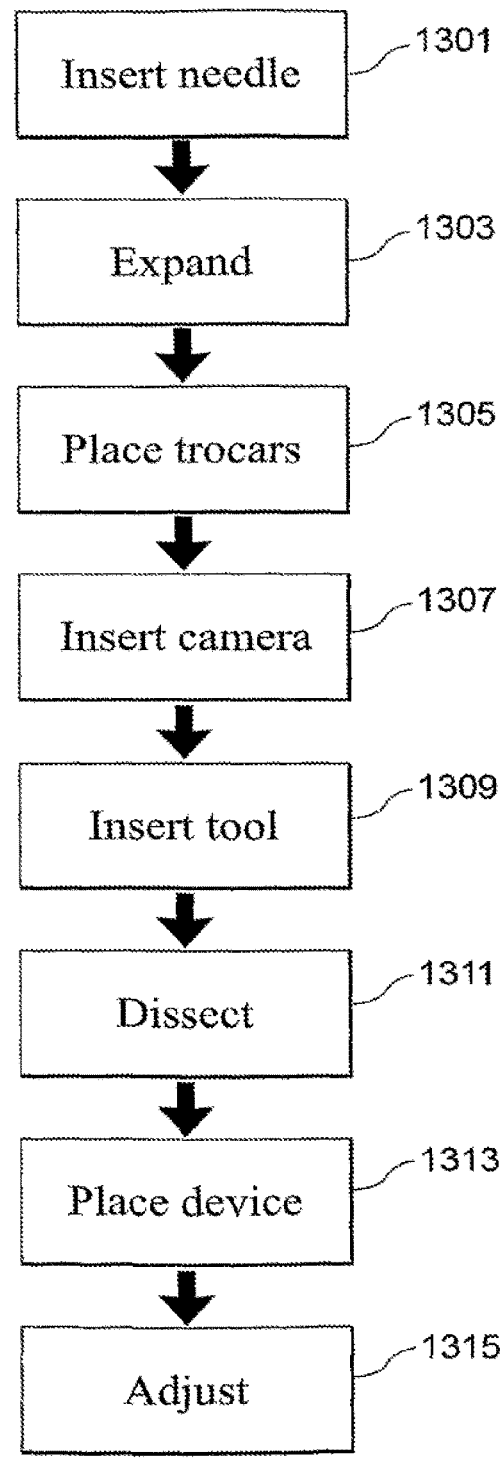

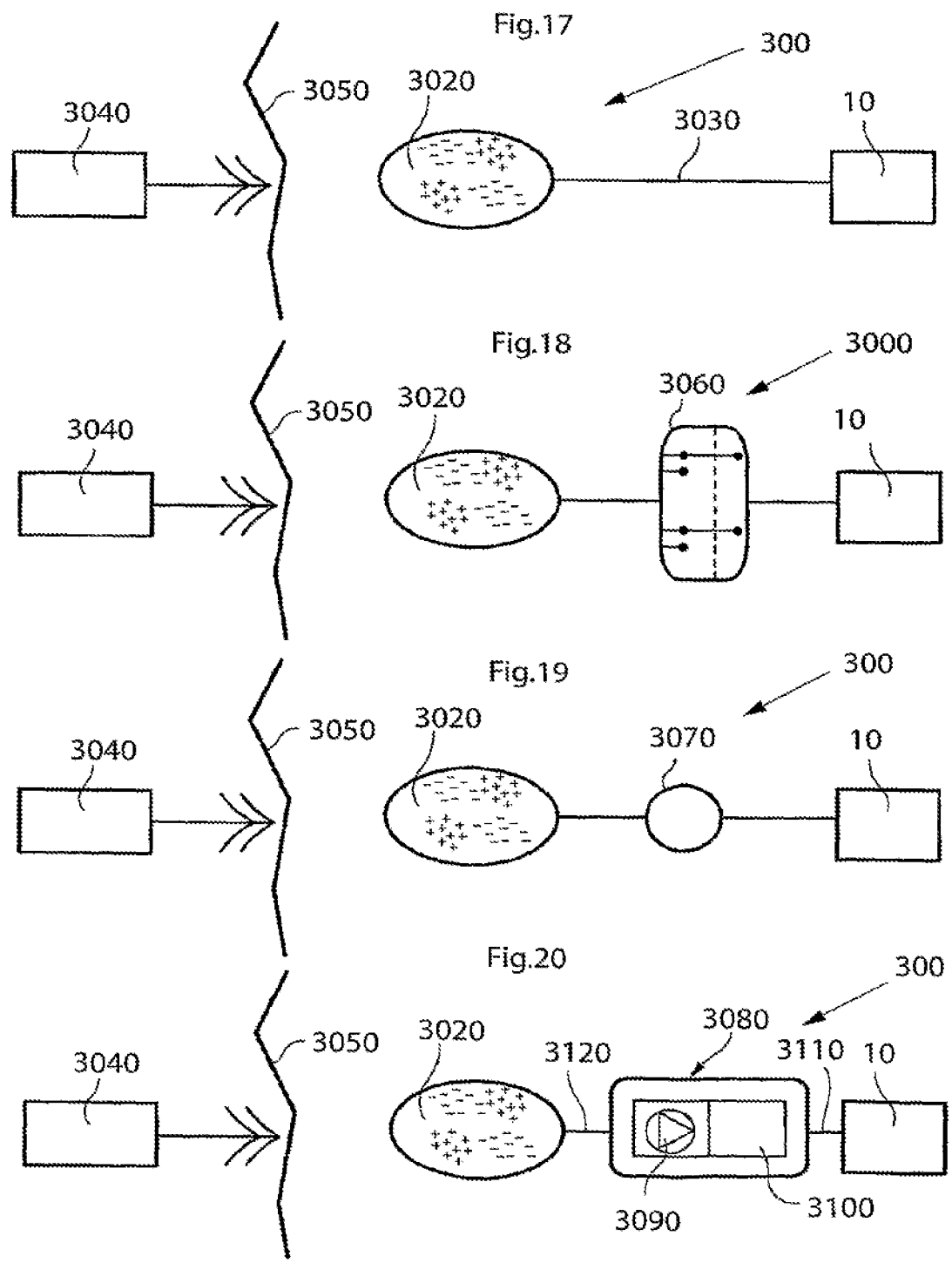

DEVICE FOR TREATMENT OF ANEURYSM

This application is a continuation of U.S. application Ser. No. 12/682,501, filed Apr. 9, 2010, now U.S. Pat. No. 9,795,320, which is the U.S. national phase of International Application No. PCT/SE08/00558, filed Oct. 10, 2008, which designated the U.S. and claims the benefit of U.S. Provisional Application No. 60/960,715, filed Oct. 11, 2007 and 60/960,716, filed Oct. 11, 2007, the entire contents of each of which are hereby incorporated by reference in this application.

TECHNICAL FIELD

The present invention relates to a method and a device for treating a vascular aneurysm of a human or mammal patient.

BACKGROUND

An aneurysm (or aneurism) is a localized, blood-filled dilation (balloon-like bulge) of a blood vessel caused by disease or weakening of the vessel wall. Aneurysms most commonly occur in arteries at the base of the brain (the circle of Willis) and in the aorta (the main artery coming out of the heart), a so-called aortic aneurysm. The bulge in a blood vessel can burst and lead to death at any time. The larger an aneurysm becomes, the more likely it is to burst and since aneurysms naturally grow, given enough time they will inevitably reach the bursting point if undetected.

Given the severe consequences of an aneurysm screening is now commonly performed in order to early detect the presence of an aneurism. In case of an aortic aneurysm the blood-filled dilation is commonly located in the abdomen close to the Y-bifurcation extending to the legs. At this location the aorta is typically about 2.5 centimeters wide, which can be measured for example using ultra-sonic or X-ray based measuring devices.

Existing treatment when detecting an aortic aneurysm includes implantation of a stent around the vessel using open surgery. An alternative surgical procedure is to implant a tube from the groin an guide the stent via arteria femoralis into position where the blood flow can by-pass the aortic aneurysm via the tube. The latter treatment has the drawback that an embolism easily is formed when introducing alien material into the bloodstream.

Hence, there exists a need for a treatment of aortic aneurysm that is more robust and which brings about fewer complications.

SUMMARY

It is an object of the present invention to overcome or at least reduce some of the problems associated with treatment and monitoring of an aneurysm.

This object and others are obtained by the method, system and device as set out in the appended claims. Thus, by providing a member around the aneurysm, the aneurysm can be treated and monitored.

In accordance with one embodiment the device is adapted to be adjusted postoperatively. Hereby the treatment can be efficiently carried out without having to perform surgery when adjusting the member.

In accordance with one embodiment the device is adapted to prevent or reduce an expansion of the aneurysm. Hereby the risk for the blood vessel to burst is significantly reduced.

In accordance with one embodiment the device is adapted to monitor an expansion an aneurysm. Hereby information relating to the aneurysm can be collected in an efficient manner and used as input in treatment and diagnosis of the aneurysm.

In accordance with one embodiment the device is adapted to perform self adjustments of the pressure applied onto said aneurysm within a predetermined treatment interval.

In accordance with one embodiment the device comprises a control unit and a sensor, and the control unit is adapted to control the pressure applied onto an aneurysm based on signals generated by the sensor.

In accordance with one embodiment the surface of the device facing the blood vessel is adapted to exercise pressure on the blood vessel. The pressure can be applied either mechanically or hydraulically.

In accordance with one embodiment the implantable member is a Y-shaped member adapted to be placed at the Aorta Bifurcation.

In accordance with one embodiment a, system comprising at least one switch implantable in the patient for manually and non-invasively controlling the device is provided.

In another preferred embodiment, the system comprises a wireless remote control for non-invasively controlling the device.

In a preferred embodiment, the system comprises a hydraulic operation device for operating the device.

In one embodiment, the system comprises comprising a motor or a pump for operating the device.

The invention also extends to methods for implanting the device and to a computer program product adapted to control the device.

Any feature in any of the four combinations of features in the combination embodiments described below may be used in any combination and furthermore in combination with any other feature or embodiment described in any of the other figures or figure text or descriptions in this application.

First combination embodiments includes electrical stimulation comprising:

A medical device including a stimulation device for treating a vascular aneurysm of a human or mammal patient comprising:

at least one implantable electrode adapted to placed in close connection to the aneurysm, the at least one electrode being adapted to provide an electrical stimulation pulse on a wall portion of the aneurysm.

At least one electrode is adapted to stimulate multiple stimulation points. Alternatively at least two electrodes are provided and wherein groups of stimulation points are controllable to be individually stimulated.

A pulse generator adapted to generate positive and negative electrical stimulation pulses.

Electrical stimulation pulses, which may have a constant current and preferable the stimulation device deliver the electrical stimulation pulse as pulse train stimulation with breaks to allow the vessel to rest.

A stimulation device that deliver the electrical stimulation pulses at different time intervals.

A device preferable delivering the electrical stimulation pulse as a pulse width modulated stimulation pulse.

A stimulation device preferable deliver the electrical stimulation pulse during the systolic phase.

A stimulation device further comprising a monitoring system for detecting an expansion of the aneurysm. Also to avoid any fast expansion and burst leading to death.

If so said monitoring system may increase intensity and or position of the stimulation, when detecting an expansion of the aneurysm.

A method of treating an aneurysm of a mammal patient by providing the medical device according to any feature disclosed herein, comprising the steps of:
inserting a needle or a tube like instrument into the patient's abdominal cavity,
using the needle or tube like instrument to fill a part of the patient's body with gas and thereby expanding said abdominal cavity,
placing at least two laparoscopic trocars in said cavity,
inserting a camera through one of the laparoscopic trocars into said cavity,
inserting at least one dissecting tool through one of said at least two laparoscopic trocars,
dissecting an area of an aneurysm of a blood vessel,
placing said medical device, comprising a stimulation device, onto said the aneurysmic blood vessel, and
stimulating said aneurysm to increase the tonus of the aneurysm wall.

An alternative method of treating an aneurysm of a mammal patient by providing the medical device including any feature disclosed herein, comprising the steps of:
inserting a needle or a tube like instrument into the patient's thoraxial cavity,
using the needle or tube like instrument to fill a part of the patient's body with gas and thereby expanding said thoraxial cavity,
placing at least two laparoscopic trocars in said cavity,
inserting a camera through one of the laparoscopic trocars into said cavity,
inserting at least one dissecting tool through one of said at least two laparoscopic trocars, dissecting an area of an aneurysm of a blood vessel,
placing said medical device, comprising a stimulation device, onto said the aneurysmic blood vessel, and
stimulating said aneurysm to increase the tonus of the aneurysm wall.

An alternative method of treating an aneurysm of a mammal patient by providing the medical device including any feature disclosed herein, said method comprising the steps of:
cutting the skin in the abdominal or thoraxial wall of said mammal patient,
dissecting an area of the aneurysm,
placing said medical device, comprising a stimulation device, onto said aneurysm, and
stimulating said aneurysm to increase the tonus of the aneurysm wall.

A method of treating an aneurysm of a mammal patient by providing the medical device including any feature disclosed herein, said method comprising the steps of:
cutting the skin of said mammal patient,
dissecting an area of the aneurysm,
placing said medical device, comprising a stimulation device, onto said aneurysm, and stimulating said aneurysm to increase the tonus of the aneurysm wall.

Additionally a computer program product comprising computer program segments that when executed on a computer causes the computer to generate a pattern of signals for an implantable electrode adapted to placed in close connection to an aneurysm, the at least one electrode being adapted to provide an electrical stimulation pulse on a wall portion of the aneurysm.

A device including a digital storage medium comprising the computer program product.

Second combination embodiments includes a hydraulic system pressure on the aneurysm comprising:

A device for treating an aneurysm of a human or mammal patient comprising:
An implantable member adapted to hold fluid, wherein said member is adapted to be placed in connection with a blood vessel having the aneurysm, the member being adapted to exercise a pressure on the aneurysm of said blood vessel.

A device preferable adapted to prevent or reduce an expansion of said aneurysm.

A device adapted to be postoperatively adjusted. The device is normally non-invasively adjustable.

A device preferable adapted to perform self adjustments of the pressure applied onto said aneurysm within a predetermined treatment interval.

A device normally comprising a control unit and a sensor, the control unit being adapted to control, pressure adjustments of based on a signal generated by the sensor.

The sensor may comprise any type of sensor. Preferable a pressure regulator is adapted to regulate the pressure in the member, wherein the pressure regulator preferable is adapted to even out the difference in pressure in the implantable member during the systolic and diastolic phase for reducing the pressure difference or providing a substantially even outside pressure on the aneurysm. The pressure regulator may comprise pressure tank.

A implantable member which is alternatively Y-shaped, wherein the implantable Y-shaped member normally is adapted to be placed at the Aorta Bifurcation A pressure regulator in one embodiment comprises an expandable first reservoir.

The expandable first reservoir preferable is spring loaded.

A device wherein the pressure regulator in a preferred embodiment comprises a pump.

A device further comprising a second reservoir and a pump adapted to move liquid between the first and second reservoirs.

A device wherein preferable said first reservoir has a predetermined optimal pressure regulation volume treatment interval and wherein said pump is adapted to pump liquid from the first to the second reservoir to keep said first reservoir within said regulation interval, when said aneurysm expands and to pump liquid from said implantable member into said first reservoir.

A device preferable provides a pressure equal or less than the diastolic blood pressure of a treated patient.

A device preferable adapted to increase the pressure on the blood vessel when the aneurysm expands.

A device comprising a control device adapted to increase the pressure on the blood vessel when the aneurysm expands more than a predetermined value, preferable during a time period.

A control unit adapted to control the expansion of said aneurysm by controlling the pressure applied on the blood vessel when the aneurysm expands.

A device preferable further comprising a sensor for sensing an expansion of the aneurysm.

A device preferable further comprising a volume control unit adapted to directly or indirectly control the volume in the implantable member based on a signal generated by the sensor for controlling an expansion of the aneurysm, wherein normally said volume control unit controls the volume in the implantable member based on a signal indicative of: flow of fluid from said implantable member or pressure in said fluid filled in said implantable member.

A device wherein the implantable member is divided into a plurality of sub-reservoirs.

A device wherein the sub-reservoirs are provided axially along the blood vessel or radially along the blood vessel.

A device wherein preferable at least one reservoir is located above said aneurysm and one reservoir is located below said aneurysm.

A device further comprising a logic circuitry for determining when the aneurysm is expanding based on the signal from the sensor.

A device further comprising an electrical pulse generator adapted to provide electrical signals for stimulation of the aneurysm wall via electrodes located on the inside of the implantable member.

A control unit adapted to vary to position of the electrical stimulation signals for stimulation of the aneurysm.

A method of treating an aneurysm of a mammal patient by providing the medical device according to any feature disclosed herein, comprising the steps of:

inserting a needle or a tube like instrument into the patient's abdominal cavity, using the needle or tube like instrument to fill a part of the patient's body with gas and thereby expanding said abdominal cavity, placing at least two laparoscopic trocars in said cavity, inserting a camera through one of the laparoscopic trocars into said cavity, inserting at least one dissecting tool through one of said at least two laparoscopic trocars, dissecting an area of an aneurysm of a blood vessel, placing the device onto said the aneurysmic blood vessel, and adjusting the pressure the device exerts onto said aneurysm.

An alternative method of treating an aneurysm of a mammal patient by providing the medical device including any feature disclosed herein, comprising the steps of:

inserting a needle or a tube like instrument into the patient's thoraxial cavity, using the needle or tube like instrument to fill a part of the patient's body with gas and thereby expanding said thoraxial cavity, placing at least two laparoscopic trocars in said cavity, inserting a camera through one of the laparoscopic trocars into said cavity, inserting at least one dissecting tool through one of said at least two laparoscopic trocars, dissecting an area of an aneurysm of a blood vessel, placing the device onto said the aneurysmic blood vessel, and adjusting the pressure said device exerts onto said aneurysm.

An alternative method of treating an aneurysm of a mammal patient by providing the medical device including any feature disclosed herein, said method comprising the steps of:

cutting the skin in the abdominal or thoraxial wall of said mammal patient, dissecting an area of the aneurysm, placing said device onto said aneurysm, and starting the stimulation device and adapted to adjust adjust any parameter related to said stimulation.

adjusting the pressure said device exerts onto said aneurysm.

adjusting the pressure said device exerts onto said aneurysm.

A computer program product comprising computer program segments that when executed on a computer causes the computer to control the pressure applied by an implantable member adapted to hold fluid and adapted to be placed in connection with a blood vessel having an aneurysm. A digital storage medium comprising the computer program product.

Third combination embodiments includes a mechanical system putting pressure on the aneurysm including any feature in any combination comprising:

A device for treating a vascular aneurysm of a human or mammal patient comprising:

An implantable member adapted to be placed in connection with a blood vessel having an aneurysm for providing a pressure from outside the blood vessel, the device being adapted to be adjusted postoperatively.

A device preferable adapted to prevent or reduce an expansion of said aneurysm.

A device adapted to monitor an expansion of said aneurysm.

The device is preferable adjustable non-invasively.

A device adapted to perform self adjustments of the pressure applied onto said aneurysm within a predetermined treatment interval.

A device comprising an control unit and a sensor, wherein the control unit is adapted to control the pressure applied onto said aneurysm based on said signal generated by the sensor.

A device, wherein the surface of the member facing the blood vessel is adapted to exercise pressure on the blood vessel.

A device, wherein the pressure on the blood vessel is mechanically exercised.

A wherein the mechanically exercised pressure is controlled hydraulically.

A device, wherein mechanical pressure on the blood vessel is directly or indirectly exercised by a motor or a pump.

A wherein the implantable member is generally cylindrical

A device, wherein the implantable member comprises a number of segments being individually adjustable.

A device, wherein the implantable member is a Y-shaped member

A device, wherein the implantable Y-shaped member is adapted to be placed at the Aorta Bifurcation.

A pressure regulating system adapted to even out the difference in pressure in the implantable reservoir in the systolic and diastolic phase to reduce the differences or to achieve a substantially even pressure affecting said aneurysm from the outside of said blood vessel.

A device, wherein the implantable member is an elastic member.

A device, wherein the elastic member is a band.

A device, wherein the elastic member is adapted to apply a pressure onto said aneurysm and has an expansion interval wherein the pressure applied is substantially constant or within an interval for treating and reducing expansion of the aneurysm.

A device, wherein the implantable member is spring loaded.

A device according to claim 1, wherein the implantable member is hydraulically operated.

A device, wherein the implantable member is pneumatically operated

A device, wherein the implantable member is adapted to exert an essentially constant pressure or a pressure reducing the pressure difference, caused by the changes in blood pressure in said blood vessel, on the aneurysm.

A device, wherein the provided pressure is equal or less than the diastolic blood pressure of a treated patient.

A device further comprising a control unit adapted to increase the pressure on the blood vessel when the aneurysm expands.

A device comprising a control device adapted to increase the pressure on the blood vessel when the aneurysm expands more than a predetermined value.

A device comprising a control device adapted to increase the pressure on the blood vessel when the aneurysm expands more than a predetermined value during a time period.

A device, further comprising a sensor or a measuring device for sensing an expansion of the aneurysm.

A device, further comprising logic circuitry for determining when the aneurysm is expanding based on a signal from a sensor or measuring device.

A device, further comprising an electrical pulse generator adapted to provide stimulation of the aneurysm wall via electrodes located on the inside of the implantable member.

A method of treating an aneurysm of a mammal patient by providing the medical device according to any feature disclosed herein, comprising the steps of:
 inserting a needle or a tube like instrument into the patient's abdominal cavity,
 using the needle or tube like instrument to fill a part of the patient's body with gas and thereby expanding said abdominal cavity,
 placing at least two laparoscopic trocars in said cavity,
 inserting a camera through one of the laparoscopic trocars into said cavity,
 inserting at least one dissecting tool through one of said at least two laparoscopic trocars,
 dissecting an area of an aneurysm of a blood vessel,
 placing the device onto said the aneurysmic blood vessel, and adjusting the pressure the device exerts onto said aneurysm.

An alternative method of treating an aneurysm of a mammal patient by providing the medical device including any feature disclosed herein, comprising the steps of:
 inserting a needle or a tube like instrument into the patient's thoraxial cavity,
 using the needle or tube like instrument to fill a part of the patient's body with gas and thereby expanding said thoraxial cavity,
 placing at least two laparoscopic trocars in said cavity,
 inserting a camera through one of the laparoscopic trocars into said cavity,
 inserting at least one dissecting tool through one of said at least two laparoscopic trocars,
 dissecting an area of an aneurysm of a blood vessel,
 placing the device onto said the aneurysmic blood vessel, and
 adjusting the pressure said device exerts onto said aneurysm.

An alternative method of treating an aneurysm of a mammal patient by providing the medical device including any feature disclosed herein, said method comprising the steps of:
 cutting the skin in the abdominal or thoraxial wall of said mammal patient,
 dissecting an area of the aneurysm,
 placing said device onto said aneurysm, and
 starting the stimulation device and adapted to adjust adjust any parameter related to said stimulation.
 adjusting the pressure said device exerts onto said aneurysm.
 adjusting the pressure said device exerts onto said aneurysm.

A computer program product comprising computer program segments that when executed on a computer causes the computer to control the pressure applied by an implantable member adapted to be placed in connection with a blood vessel having an aneurysm.

A digital storage medium comprising the computer program product.

Fourth combination embodiments includes a monitoring/sensor system putting pressure on the aneurysm including any feature in any combination, comprising:
 A device for monitoring an aneurysm of a human or mammal patient comprising:
 A sensor placed in relation to a wall portion of the aneurysm for generating a signal corresponding to a parameter related to the aneurysm or the treatment of the aneurism.

A device, wherein the parameter corresponds to the size of the aneurysm.

A device, wherein the parameter corresponds to the diameter of the aneurysm.

A device wherein the sensor is a gauge sensor.

A device wherein the parameter corresponds to a pressure.

A device wherein the pressure corresponds to a pressure from a hydraulic cuff provided around the aneurysm.

A device wherein the pressure corresponds to a pressure from a mechanical implantable member provided around the aneurysm.

A device wherein the pressure corresponds to a pressure in a blood vessel.

A device wherein the sensor is adapted to measure the pressure exerted on an implantable member provided around the aneurysm.

A device wherein the sensor is adapted to measure the volume of a hydraulic implantable member.

A method of treating an aneurysm of a mammal patient by providing the medical device, comprising the steps of:
 inserting a needle or a tube like instrument into the patient's abdominal cavity,
 using the needle or tube like instrument to fill a part of the patients body with gas and thereby expanding said abdominal cavity,
 placing at least two laparoscopic trocars in said cavity,
 inserting a camera through one of the laparoscopic trocars into said cavity,
 inserting at least one dissecting tool through one of said at least two laparoscopic trocars,
 dissecting an area of an aneurysm of a blood vessel,
 placing the device onto said the aneurysmic blood vessel, and
 monitoring the expansion of the aneurysm by measuring the expansion the aneurysm exerts onto the device.

A method of treating an aneurysm of a mammal patient by providing the medical device, comprising the steps of:
 inserting a needle or a tube like instrument into the patient's thoraxial cavity,
 using the needle or tube like instrument to fill a part of the patient's body with gas and thereby expanding said thoraxial cavity,
 placing at least two laparoscopic trocars in said cavity,
 inserting a camera through one of the laparoscopic trocars into said cavity,
 inserting at least one dissecting tool through one of said at least two laparoscopic trocars,
 dissecting an area of an aneurysm of a blood vessel,
 placing the device onto said the aneurysmic blood vessel, and
 monitoring the expansion of the aneurysm by measuring the expansion the aneurysm exerts onto the device.

A method of treating an aneurysm of a mammal patient by providing the medical device, said method comprising the steps of:
cutting the skin in the abdominal or thoraxial wall of said mammal patient,
dissecting an area of the aneurysm,
placing said device onto said aneurysm, and
monitoring the expansion of the aneurysm by measuring the expansion the aneurysm exerts onto the device.

A method of treating an aneurysm of a mammal patient by providing the medical device, said method comprising the steps of:
cutting the skin of said mammal patient,
dissecting an area of the aneurysm,
placing said device onto said aneurysm, and
monitoring the expansion of the aneurysm by measuring the expansion the aneurysm exerts onto the device.

BRIEF DESCRIPTION OF THE DRAWINGS

The present invention will now be described in more detail by way of non-limiting examples and with reference to the accompanying drawings, in which:

FIG. 12 is a flowchart illustrating steps performed when implanting a device for treating or monitoring an aneurysm in accordance with one embodiment, FIG. 13 is a flowchart illustrating steps performed when implanting a device for treating or monitoring an aneurysm in accordance with one embodiment.

FIGS. 17-31 schematically show various embodiments of the system for wirelessly powering the device shown in FIG. 16.

DETAILED DESCRIPTION

Figure 1:
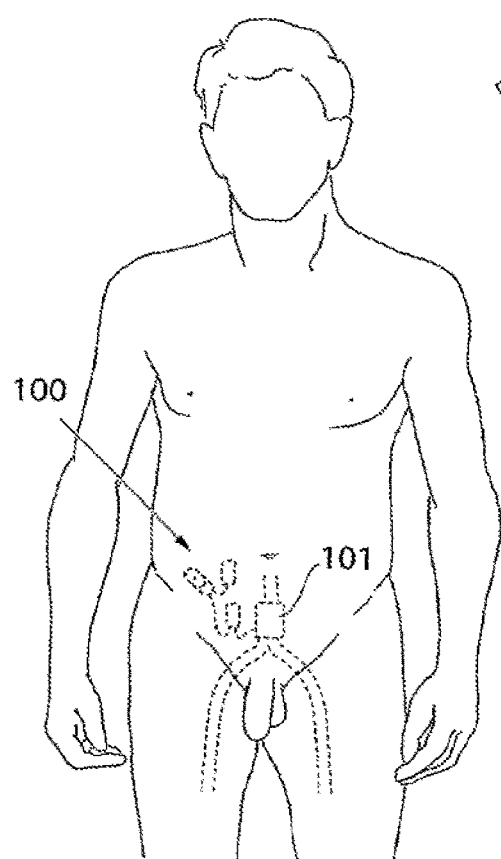
FIG. 1 is general view of a human body having a device for treating aneurysm implanted.

In FIG. 1 a general view of a human 100 having a member, in particular a cuff 101, implanted for treating an aneurism is shown. In FIG. 1 the treated aneurism is located on the aorta in the abdomen close to the Y-bifurcation extending to the legs. The cuff 101 can be designed in various ways but is generally formed as an implantable member adapted to be placed in connection with a blood vessel having said vascular aneurysm, and adapted to exert a pressure on said aneurysm from the outside of said blood vessel. In particular the pressure exerted on the blood vessel is essentially uniform from all direction and adapted to hinder the blood vessel to expand in all directions thereby acting to prevent the blood vessel from bursting. The pressure can in accordance with one embodiment be essentially equal to or lower than the diastolic blood pressure of the treated patient. The cuff 101 can be made in any suitable material such as an elastic material adapted for implantation in a human or mammal body.

The cuff 101 can exercise the pressure in a number of different ways. In accordance with one embodiment of the present invention the pressure applied on the blood vessel can be mechanical and adjustable by means of an adjustable screw or a similar means in order to apply a pressure on the blood vessel. The cuff 101 can also be formed by a spring loaded member and operated in a suitable manner such as hydraulically or pneumatically.

Figure 2:
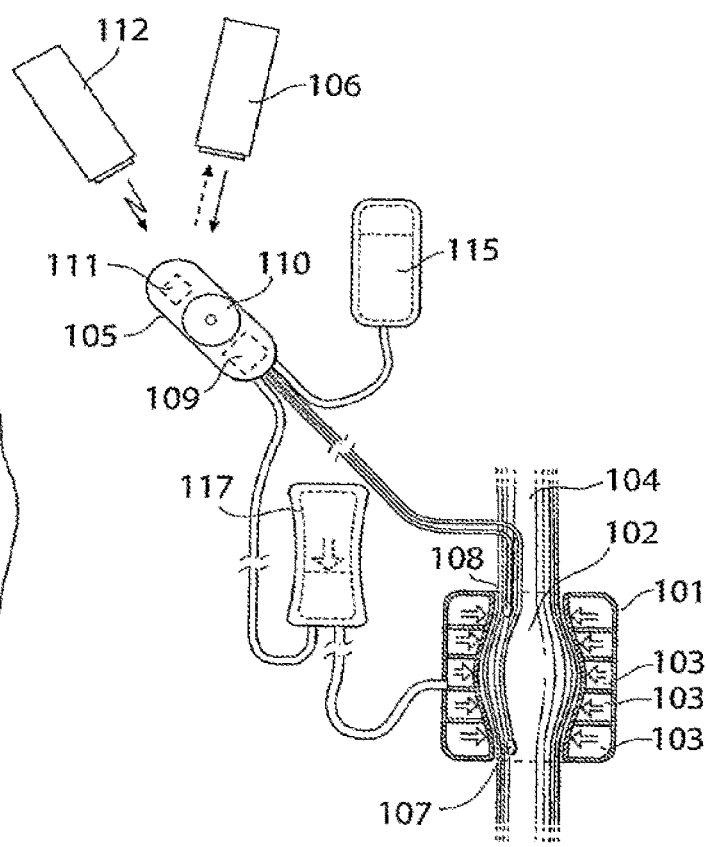
FIG. 2 is a view illustrating a device for treating aneurysm with associated equipment.

In FIG. 2 a cuff 101 in accordance with one embodiment of the present invention is shown in more detail. The cuff 101 comprises a number of segments 103 each adjustable and possible to tailor to fit a particular aneurism 102 of a blood vessel 104 to be treated. Each segment 103 can be adjusted either as a whole or individually. The segments 103 can be controlled and adjusted mechanically by an adjustable screw or similar or adapted to be filled with a fluid. For example, the segments can be provided axially along the blood vessel and also radially along the blood vessel forming a matrix of sub-segments that constitutes the cuff 101. In particular one segment can be located above and one below the aneurysm along the blood vessel.

The adjustment can be controlled by an electronic control unit 105 adapted to receive and transmit signals from a transmitter/receiver 106 located outside the body of a treated patient. The electronic control unit can also comprise a chargeable battery 111 chargeable from the outside by an external charger unit 112. The electronic control unit can comprise an electrical pulse generator 109 for generating electrical pulses as is described in more detail below.

The electronic control unit, such as a microprocessor or a MCU or a FPGA or a ASIC and 105 can further be connected to or comprise a hydraulic pump 110 associated with a reservoir 115 containing of a fluid used to regulate the pressure of the cuff 101. The pump is thus adapted to pump the hydraulic fluid in or out from the cuff 101 in order to adjust the pressure applied in the aneurism. The control mechanism used for keeping the pressure in the cuff 101 can comprise a pressure tank 117.

In a preferred embodiment the pressure tank 117 is adapted to be able to change its volume still keeping substantially the same pressure, thus keeping the same pressure onto the aneurysm although some expansion of size of the aneurysm may occur. However, if the expansion goes too far the pressure tank may come out of range to keep the pressure constant and with some kind of volume detection in the pressure tank the pump 110 is then able to move fluid out from the pressure tank into the reservoir 115 to again be within pressure range in the pressure tank. The pressure tank is also able to even out the systolic pulses supplied to the aneurysmic wall.

The cuff 101 can be shaped in any desirable form to enable treatment of an aneurism wherever it is located. In accordance with one embodiment the cuff 101 is provided with at least one sensor 107 adapted to sense the pressure from the blood vessel that the cuff is surrounding.

The sensor(s) 107 used to generate a signal indicative of one or many parameters related to the aneurism and the device 101 used for treating the aneurism can for example be a gauge sensor. The sensor 107 can be adapted to generate sensor signals used for monitoring parameters including but not limited to the pressure in a hydraulic cuff the pressure of a mechanical cuff, the pressure of a pneumatic cuff, the pressure in a blood vessel, the shape of the blood vessel in particular a parameter related to the diameter of the aneurysm.

An alternative or complement to the remote placed transmitter 106 is a switch (part of 105), preferable subcutaneously placed, such a switch may be mechanical or electrical, such as a microprocessor or a MCU or a FPGA or a ASIC, or the switch may comprise a small hydraulic control reservoir.

The restriction device may comprise any hydraulic device or mechanical device or stimulation device alone or monitoring/sensor device in any combination as described in the present application. The stimulation device may comprise both thermal stimulation or electrical stimulation. If a hydraulic system is used the hydraulic pump may in a system comprise an injection port (part of 110) for the injection of hydraulic fluid, preferable for calibration of hydraulic fluid. A subcutaneously place switch may also be used as well as an feed back alarm system connected to the sensor/monitoring system.

Although the device has specific placements on the drawings it should be understood that the placement might vary.

Any combination of features or embodiments may comprise from any source within this application. Any embodiment in any combination that is disclosed in this application, specially, but not limited to, in FIG. 1-42, may be used.

Figure 3:
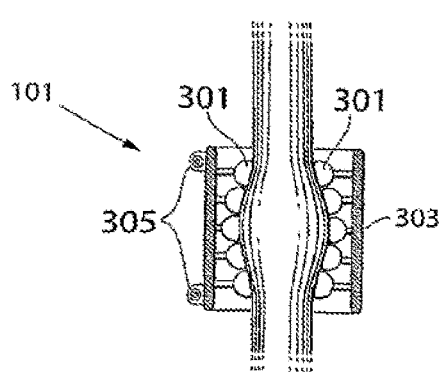
FIG. 3 is a view illustrating a mechanical device far treating aneurysm.

In FIG. 3 a view illustrating a mechanical cuff 101 is shown. The cuff can for example comprise an elastic material 301 kept in place by a suitable compressing device. The cuff 101 in accordance with one embodiment of the present invention comprises an elastic material in the form of a number of gel filled pads 301. The pads 301 can be shaped in a suitable manner and in particular formed to absorb the geometrical shape of the aneurysm. This can for example be achieved by providing pads with different tilting angles. The elastic material 301 can be kept in place by at least one adjustable fastening member 303. The fastening member 303 can for example be adjusted by a screw 305 or a similar device. By adjusting the fastening member 303 the pressure applied on the aneurysm can be controlled.

Figure 4:
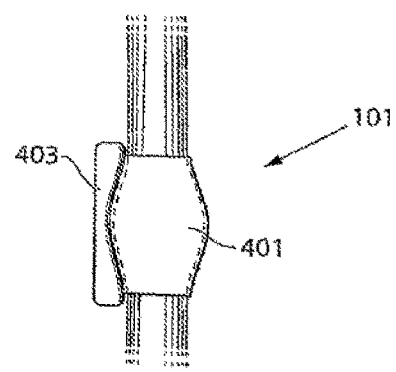
FIG. 4 is a view illustrating a mechanical device for treating aneurysm.

In FIG. 4, a view illustrating a mechanical cuff 101 is shown. The cuff can for example comprise an elastic band 401. The hand 401 can be adjusted by an adjustor 403 to provide a higher or smaller pressure on the aneurysm.

Figure 5:
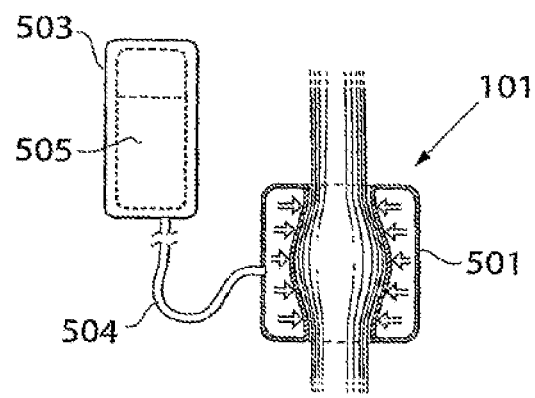
FIG. 5 is a view illustrating a hydraulic device for treating aneurysm.

In FIG. 5, a view illustrating a hydraulic cuff 101 is shown. The cuff can for example comprise implantable member 501 adapted to hold fluid. The member 501 is adapted to be placed in connection with a blood vessel having an aneurysm. The member can exercise a pressure on the aneurysm the blood vessel in response to the conditions of the fluid of the member 501. By filling the member with a fluid pressure can be applied onto the aneurysm in order to prevent or reduce an expansion the aneurysm when implanted in a patient thereby enabling postoperative treatment of the aneurysm. Further the treatment can be adjusted postoperatively by regulating the pressure using an implanted pressure regulator 503. The pressure regulator can for example be formed by a pressure tank 503 implanted in the patient interconnected via a hose 504 with the member 501. The pressure tank can comprise an expandable reservoir 505 for storing superfluous fluid.

Figure 6:
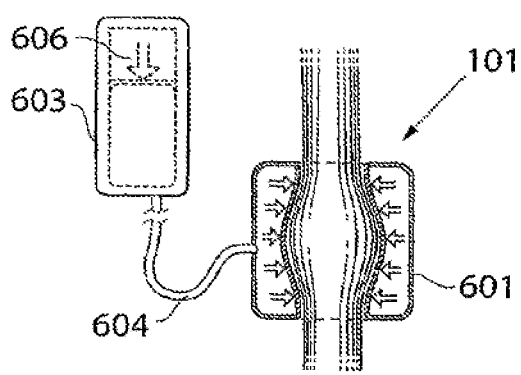
FIG. 6 is a view illustrating a hydraulic device for treating aneurysm.

In FIG. 6, a view illustrating a hydraulic cuff 101 is shown. The cuff can for example comprise implantable member 601 adapted to hold fluid. The member 601 is adapted to be placed in connection with a blood vessel having an aneurysm. The member can exercise a pressure on the aneurysm the blood vessel in response to the conditions of the fluid of the member 601. By filling the member with a fluid pressure can be applied onto the aneurysm in order to prevent or reduce an expansion the aneurysm when implanted in a patient thereby enabling postoperative treatment of the aneurysm. Further the treatment can be adjusted postoperatively by regulating the pressure using an implanted pressure regulator 603. The pressure regulator can for example be formed by a spring loaded tank 603 implanted in the patient interconnected via a hose 604 with the member 601. The spring 606 used to control the pressure of the tank and thereby indirectly the pressure applied by the cuff 101 on the aneurysm can be an adjustable spring in order to control the pressure.

Figure 7:
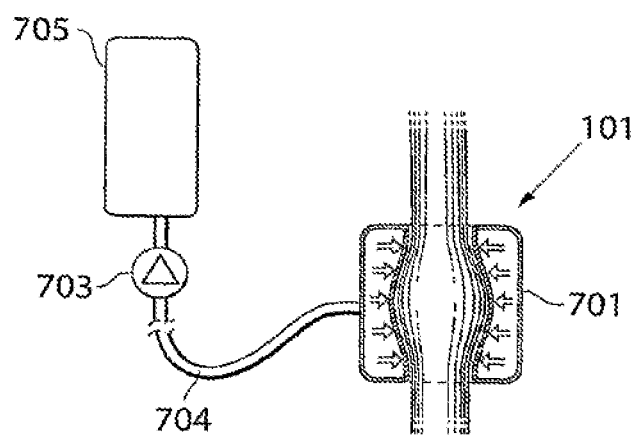
FIG. 7 is a view illustrating a hydraulic device for treating aneurysm.

In FIG. 7, a dew illustrating a hydraulic cuff 101 is shown. The cuff can for example comprise implantable member 701 adapted to hold fluid. The member 601 is adapted to be placed in connection with a blood vessel having an aneurysm. The member can exercise a pressure on the aneurysm the blood vessel in response to the conditions of the fluid of the member 701. By filling the member with a fluid pressure can be applied onto the aneurysm in order to prevent or reduce an expansion the aneurysm when implanted in a patient thereby enabling postoperative treatment of the aneurysm. Further the treatment can be adjusted postoperatively by regulating the pressure using an implanted pressure regulator 703. The pressure regulator can for example be formed by a pump 703 implanted in the patient on a hose 704 interconnecting a tank 705 with the member 701. The pump 703 is used to control the pressure of the member 703 by pumping fluid in and out of the member 701 and thereby controlling the pressure applied by the cuff 101 on the aneurysm.

By sensing the pressure from the blood vessel the cuff can be controlled to apply a correct pressure on the blood vessel thereby keeping the form of the blood vessel essentially constant. For example the pressure may vary over time as a result of changes in the wall of the blood vessel of surrounding tissue. Also the pressure will change as a function of the phase in which the heart is working. In other words the pressure will be different in a systolic phase as compared to a diastolic phase. By using a pressure sensor the pressure applied by the cuff 101 can be adapted to react to changes in the sensed pressure and apply a corresponding counter pressure. The sensor signals generated by the sensor(s) 107 of the cuff can also be used to trigger an alarm in response to the sensor signal indicating an expansion of the aneurism. In response to an alarm signal being generated the cuff can be automatically controlled to exercise a counter pressure on the blood vessel to counter or limit the expansion of the aneurism.

In yet another embodiment, electrodes 108 can be provided in the cuff. The electrodes can be connected to the electrical pulse generator, which is adapted to generate electrical pulses for stimulating the wall of the aneurism. The purpose of the electrical stimulation is to increase the tonus of the wall of the aneurism.

Figure 8:
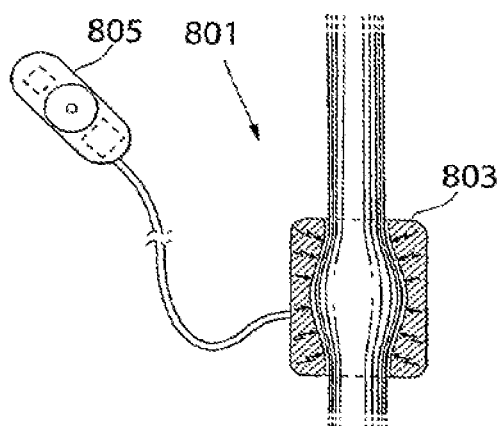
FIG. 8 is a view illustrating a stimulation device for treating a vascular aneurysm of a human or mammal patient.

In FIG. 8, a stimulation device 801 for treating a vascular aneurysm of a human or mammal patient is shown. The device 801 comprises at least one implantable electrode 803 adapted to be placed in close connection to the aneurism. The electrode is adapted to provide an electrical stimulation pulse on a wall portion of the aneurysm. The electrical stimulation pulse can for example be generated by a pulse generator 805. The pulse generator can be implanted in the patient.

In accordance with one embodiment the electrical stimulation device used for treating a vascular aneurysm of a human or mammal patient is connected to electrodes adapted to stimulate the wall of the aneurism at multiple stimulation points. The multiple stimulation groups may further be organized in different stimulation, groups which can stimulated independently of each other. In accordance with one embodiment the electrical stimulation is performed with positive and or negative voltage stimulation pulses. In one embodiment the current used for stimulation of the aneurysm wall is kept essentially constant.

The sequence of electrical pulses used to stimulation the wall of the aneurysm can be applied with a predetermined periodicity having periods of no stimulation therein between during which periods without stimulation the wall of the aneurysm is allowed to rest. The electrical stimulation signal can also be Pulse Width Modulated to control the energy applied. In accordance with one embodiment the electrical stimulation is applied during the systolic phase to increase the tonus of the wall of the aneurysm. The systolic phase can be detected by the sensors 107 used to sense the pressure of the aneurysm as described above.

In accordance with one embodiment the stimulation can be controlled to be applied with a temporarily increased intensity and position during emergency situations when the aneurysm is detected to rapidly expands, to limit the expansion of said aneurysm.

Figure 9:
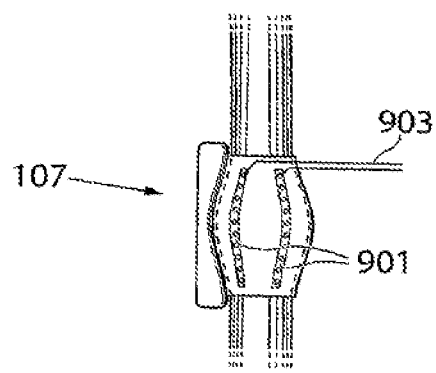
FIG. 9 is a view illustrating a sensor used when treating or monitoring a vascular aneurysm of a human or mammal patient.

In order to provide input for controlling the pressure and or to monitor the aneurysm a device 107 can be provided. In FIG. 9 a view illustrating a sensor 901 used when treating or monitoring a vascular aneurysm of a human or mammal patient is shown. The sensor 901 is placed in relation to a wall portion of the aneurysm for generating a signal corresponding to a parameter related to the aneurysm or the treatment of the aneurism. The signal generated by the sensor can be a signal corresponding to the sire of the aneurysm and is accessible via a signal output 903. For example the signal can be indicative of the diameter of the aneurysm. In accordance with one embodiment of the he sensor is a gauge sensor. The sensor 901 can also be adapted to generate any output related to monitoring or treatment of the aneurysm. For example the sensor can be adapted to sense the resistance, capacitance, pressure, volume extension, flexure of a member in contact with the aneurysm.

Figure 10:
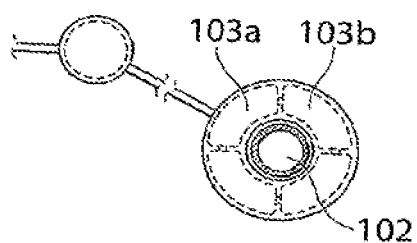
FIG. 10 is a view from above of a device for treating aneurysm implanted around a blood vessel.
Figure 11:
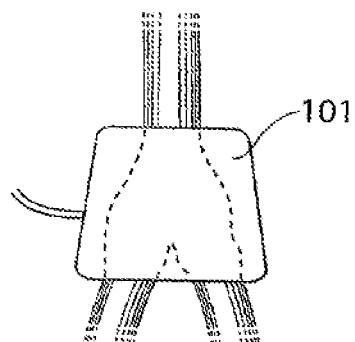
FIG. 11 is a view of a device for treating aneurysm having a Y-shape.

The shape of the cuff 101 can as stated above be tailor made to suit the location where an aneurysm is to be treated. In FIG. 10, a cuff 101 is seen from above in a direction aligned with a treated blood vessel. As can be seen in FIG. 3 each segment 3 can be sub-divided into a number of sub segments 103a, 103b . . . together forming a closed loop around the treated aneurysm. In case the aneurysm is located in the aorta bifurcation region the cuff 101 can be Y-shaped as is shown in FIG. 11.

The device as described herein can be implanted in a patient using some suitable surgical procedure as depicted in FIG. 12. For example, the device can be implanted by inserting a needle or a tube like instrument into the patient's abdominal cavity, step 1201. Next in a step 1203 a part of the patient's body with gas using the needle or tube like instrument thereby expanding said abdominal cavity. Next in a step 1205 at least two laparoscopic trocars are placed in the cavity. Thereupon in a step 1207 a camera is inserted through one of the laparoscopic trocars into the cavity. Next in a step 1209 at least one dissecting tool is inserted through one of said at least two laparoscopic trocars. An area of an aneurysm of a blood vessel is then dissected in a step 1211. The device is then placed onto the aneurysmic blood vessel in a step 1213, and the pressure that the device exerts onto the aneurysm is adjusted in a step 1215.

In accordance with one embodiment of the present invention the device can be implanted by a procedure depicted in FIG. 13. First in a step 1301 a needle or a tube like instrument is inserted into the patient's thoraxial cavity. Next, in a step 1303 a part of the patient's body with gas using the needle or tube like instrument to fill and thereby expanding the thoraxial cavity. Thereupon at least two laparoscopic trocars are placed in said cavity in a step 1305 Thereupon in a step 1307 a camera is inserted through one of the laparoscopic trocars into the cavity. Next in a step 1309 at least one dissecting tool is inserted through one of said at least two laparoscopic trocars. An area of an aneurysm of a blood vessel is then dissected in a step 1311. The device is then placed onto the aneurysmic blood vessel in a step 1313, and the pressure that the device exerts onto the aneurysm is adjusted in a step 1315.

Figure 14:
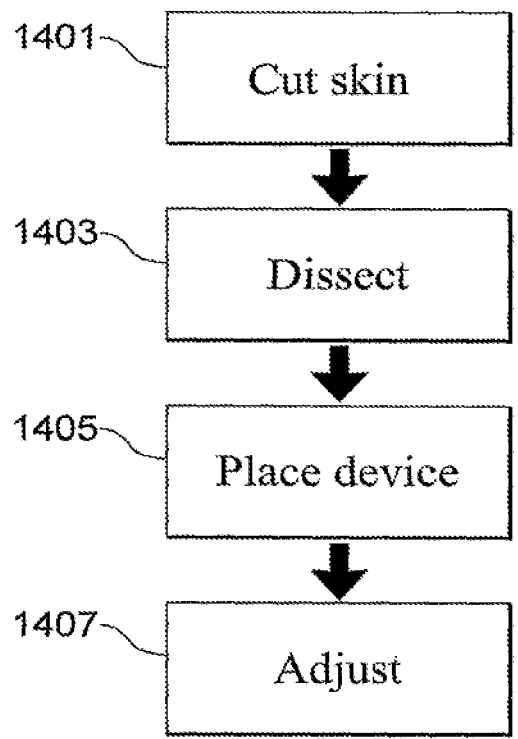
FIG. 14 is a flowchart illustrating steps performed when implanting a device for treating or monitoring an aneurysm in accordance with one embodiment.

In accordance with one embodiment of the present invention the device can be implanted by a procedure depicted in FIG. 14. First in a step 1401, the skin in the abdominal or thoraxial wall of the mammal patient is cut. Next, in a step 1403 an area of the aneurysm is dissected. Next, the device is then placed onto the aneurysmic blood vessel in a step 1405, and the pressure that the device exerts onto the aneurysm is adjusted in a step 1407.

Figure 15:
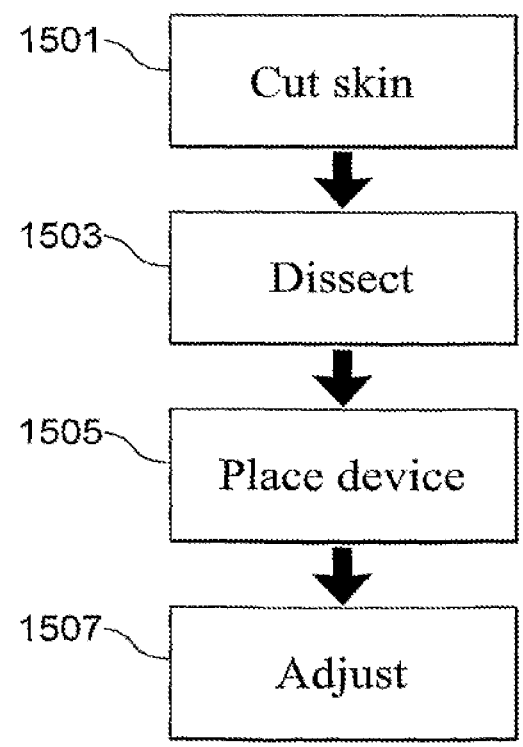
FIG. 15 is a flowchart illustrating steps performed when implanting a device for treating or monitoring an aneurysm in accordance with one embodiment.

In accordance with one embodiment of the present invention the device can be implanted by a procedure depicted in FIG. 15. First in a step 1501, the skin of the mammal patient is cut. Next, in a step 1503 an area of the aneurysm is dissected. Next, the device is then placed onto the aneurysmic blood vessel in a step 1505, and the pressure that the device exerts onto the aneurysm is adjusted in a step 1507.

Figure 16:
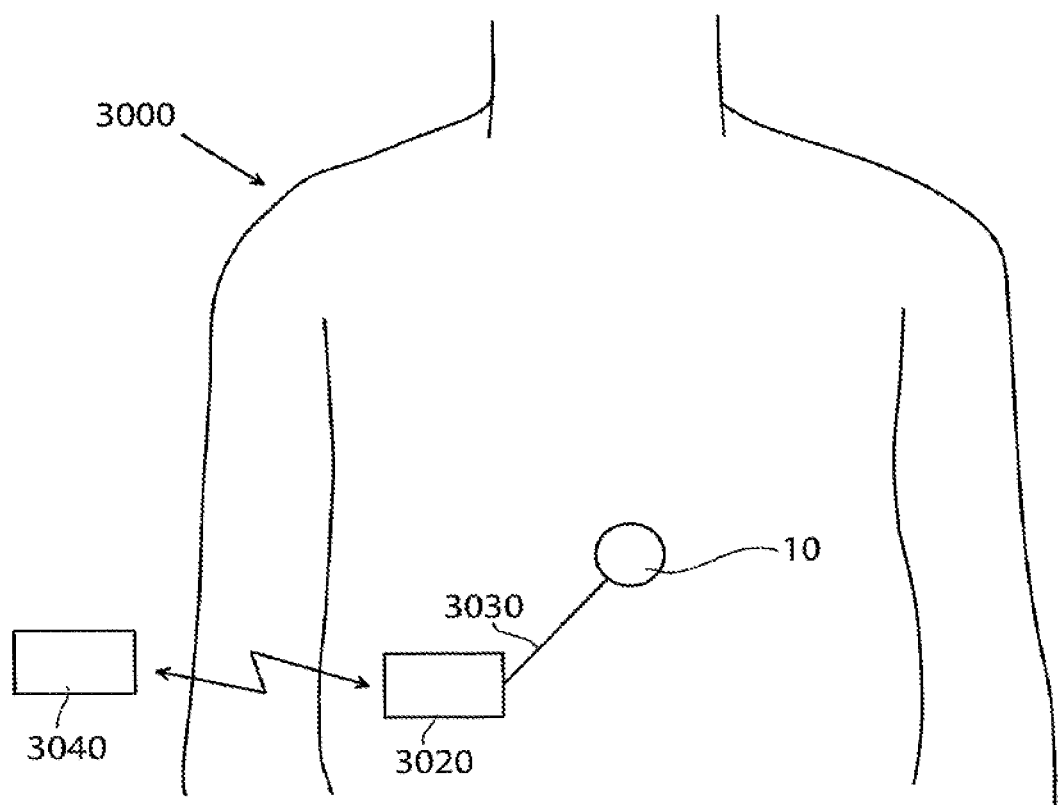
FIG. 16 illustrates a system for treating a disease, wherein the system includes a device of the invention implanted in a patient.

FIG. 16 illustrates a system for treating a disease comprising a device 10 of the present invention placed in the abdomen of a patient. An implanted energy-transforming device 3020 is adapted to supply energy consuming components of the device with energy via a power supply line 3030. An external energy-transmission device 3040 for non-invasively energizing the device 10 transmits energy by at least one wireless energy signal. The implanted energy-transforming device 10020 transforms energy from the wireless energy signal into electric energy which is supplied via the power supply line 3030.

In one embodiment at least one battery may be a part of or replace the energy transforming device 3020 to supply energy to the device 10 over a power supply line 3030. In one embodiment the battery is not rechargeable. In an alternative embodiment the battery is rechargeable. The battery supply may of course be placed both remote to and incorporated in the device.

The wireless energy signal may include a wave signal selected from the following: a sound wave signal, an ultrasound wave signal, an electromagnetic wave signal, an infrared light signal, a visible light signal, an ultra violet light signal, a laser light signal, a micro wave signal, a radio wave signal, an x-ray radiation signal and a gamma radiation signal. Alternatively, the wireless energy signal may include an electric or magnetic field, or a combined electric and magnetic field.

The wireless energy-transmission device 3040 may transmit a carrier signal for carrying the wireless energy signal. Such a carrier signal may include digital, analogue or a combination of digital and analogue signals. In this case, the wireless energy signal includes an analogue or a digital signal, or a combination of an analogue and digital signal.

Generally speaking, the energy-transforming device 3020 is provided for transforming wireless energy of a first form transmitted by the energy-transmission device 3040 into energy of a second form, which typically is different from the energy of the first form. The implanted device 10 is operable in response to the energy of the second form. The energy-transforming device 3020 may directly power the device with the second form energy, as the energy-transforming device 3020 transforms the first form energy transmitted by the energy-transmission device 3040 into the second form energy. The system may further include an implantable accumulator, wherein the second form energy is used at least partly to charge the accumulator.

Alternatively, the wireless energy transmitted by the energy-transmission device 3040 may be used to directly power the device, as the wireless energy is being transmitted by the energy-transmission device 3040. Where the system comprises an operation device for operating the device, as will be described below, the wireless energy transmitted by the energy-transmission device 1004 may be used to directly power the operation device to create kinetic energy for the operation of the device.

The wireless energy of the first form may comprise sound waves and the energy-transforming device 3020 may include a piezo-electric element for transforming the sound waves into electric energy. The energy of the second form may comprise electric energy in the form of a direct current or pulsating direct current, or a combination of a direct current and pulsating direct current, or an alternating current or a combination of a direct and alternating current. Normally, the device comprises electric components that are energized with electrical energy. Other implantable electric components of the system may be at least one voltage level guard or at least one constant current guard connected with the electric components of the device.

Optionally, one of the energy of the first form and the energy of the second form may comprise magnetic energy, kinetic energy, sound energy, chemical energy, radiant energy, electromagnetic energy, photo energy, nuclear energy or thermal energy. Preferably, one of the energy of the first form and the energy of the second form is non-magnetic, non-kinetic, non-chemical, non-sonic, non-nuclear or non-thermal.

The energy-transmission device may be controlled from outside the patient's body to release electromagnetic wireless energy, and the released electromagnetic wireless energy is used for operating the device. Alternatively, the energy-transmission device is controlled from outside the patient's body to release non-magnetic wireless energy, and the released non-magnetic wireless energy is used for operating the device.

The external energy-transmission device 3040 also includes a wireless remote control having an external signal transmitter for transmitting a wireless control signal for non-invasively controlling the device. The control signal is received by an implanted signal receiver which may be incorporated in the implanted energy-transforming device 3020 or be separate there from.

The wireless control signal may include a frequency, amplitude, or phase modulated signal or a combination thereof. Alternatively, the wireless control signal includes an analogue or a digital signal, or a combination of an analogue and digital signal. Alternatively, the wireless control signal comprises an electric or magnetic field, or a combined electric and magnetic field.

The wireless remote control may transmit a carrier signal for carrying the wireless control signal. Such a carrier signal may include digital, analogue or a combination of digital and analogue signals. Where the control signal includes an analogue or a digital signal, or a combination of an analogue and digital signal, the wireless remote control preferably transmits an electromagnetic carrier wave signal for carrying the digital or analogue control signals.

FIG. 17 illustrates the system of FIG. 16 in the form of a more generalized block diagram showing the device 10, the energy-transforming device 3020 powering the device 10 via power supply line 3030, and the external energy-transmission device 3040. The patient's skin 3050, generally shown by a vertical line, separates the interior of the patient to the right of the fine from the exterior to the left of the line.

FIG. 18 shows an embodiment of the invention identical to that of FIG. 17, except that a reversing device in the form of an electric switch 3060 operable for example by polarized energy also is implanted in the patient for reversing the device 10. When the switch is operated by polarized energy the wireless remote control of the external energy-transmission device 3040 transmits a wireless signal that carries polarized energy and the implanted energy-transforming device 3020 transforms the wireless polarized energy into a polarized current for operating the electric switch 3060. When the polarity of the current is shifted by the implanted energy-transforming device 3020 the electric switch 3060 reverses the function performed by the device 10.

FIG. 19 shows an embodiment of the invention identical to that of FIG. 17, except that an operation device 3070 in in the patient for operating the device 10 is provided between the implanted energy-transforming device 3020 and the device 10. This operation device can be in the form of a motor 3070, such as an electric servomotor. The motor 3070 is powered with energy from the implanted energy-transforming device 3020, as the remote control of the external energy-transmission device 3040 transmits a wireless signal to the receiver of the implanted energy-transforming device 3020.

FIG. 20 shows an embodiment of the invention identical to that of FIG. 17, except that it also comprises an operation device is in the form of an assembly 3080 including a motor/pump unit 3090 and a fluid reservoir 3100 is implanted in the patient. In this case the device 10 is hydraulically operated, i.e. hydraulic fluid is pumped by the motor/pump unit 3090 from the fluid reservoir 3100 through a conduit 3110 to the device 10 to operate the device, and hydraulic fluid is pumped by the motor/pump unit 3090 back from the device 10 to the fluid reservoir 3100 to return the device to a starting position. The implanted energy-transforming device 1002 transforms wireless energy into a current, for example a polarized current, for powering the motor/pump unit 1009 via an electric power supply line 3120.

Instead of a hydraulically operated device 10, it is also envisaged that the operation device comprises a pneumatic operation device. In this case, the hydraulic fluid can be pressurized air to be used for regulation and the fluid reservoir is replaced by an air chamber.

In all of these embodiments the energy-transforming device 3020 may include a rechargeable accumulator like a battery or a capacitor to be charged by the wireless energy and supplies energy for any energy consuming part of the system.

As an alternative, the wireless remote control described above may be replaced by manual control of any implanted part to make contact with by the patient's hand most likely indirect, for example a press button placed under the skin.

Figure 21:
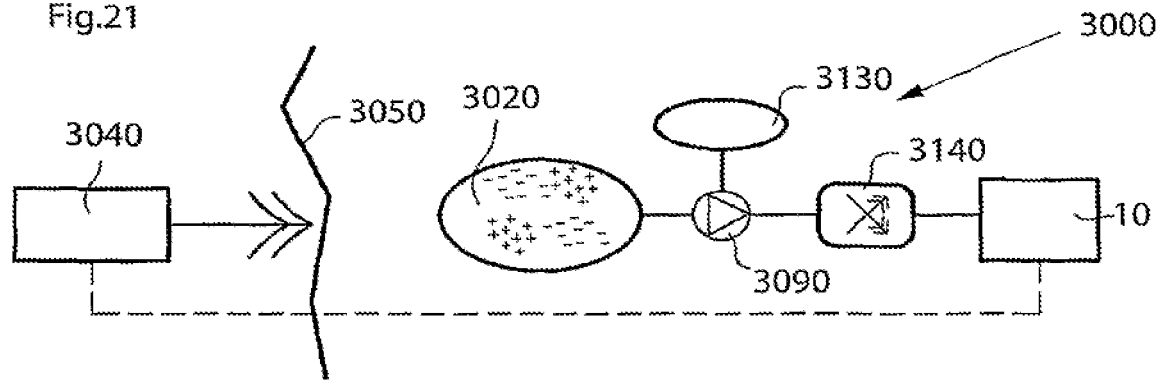

FIG. 21 shows an embodiment of the invention comprising the external energy-transmission device 3040 with its wireless remote control, the device 10, in this case hydraulically operated, and the implanted energy-transforming device 3020, and further comprising a hydraulic fluid reservoir 3130, a motor/pump unit 3090 and an reversing device in the form of a hydraulic valve shifting device 3140, all implanted in the patient. Of course the hydraulic operation could easily be perforated by just changing the pumping direction and the hydraulic valve may therefore be omitted. The remote control may be a device separated from the external energy-transmission device or included in the same. The motor of the motor/pump unit 3090 is an electric motor. In response to a control signal from the wireless remote control of the external energy-transmission device 3040, the implanted energy-transforming device 3020 powers the motor/pump unit 3090 with energy from the energy carried by the control signal, whereby the motor/pump unit 3090 distributes hydraulic fluid between the hydraulic fluid reservoir 3130 and the device 10. The remote control of the external energy-transmission device 3040 controls the hydraulic valve shifting device 3140 to shift the hydraulic fluid flow direction between one direction in which the fluid is pumped by the motor/pump unit 3090 from the hydraulic fluid reservoir 3130 to the device 10 to operate the device, and another opposite direction in which the fluid is pumped by the motor/pump unit 3090 back from the device 10 to the hydraulic fluid reservoir 3130 to return the device to a starting position.

Figure 22:
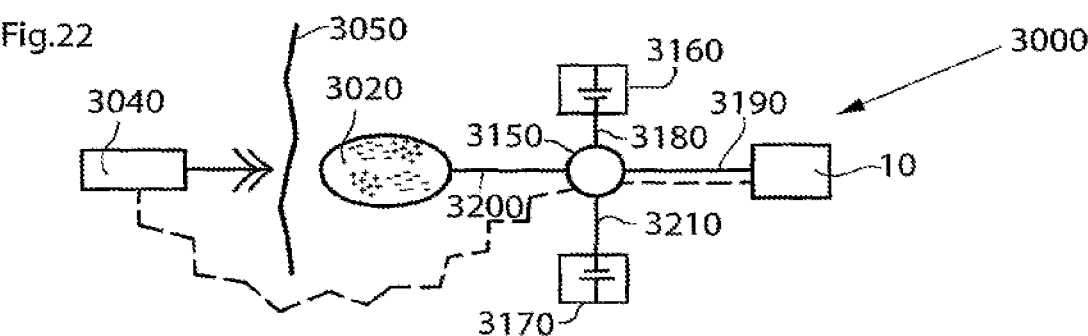

FIG. 22 shows an embodiment of the invention comprising the external energy-transmission device 1004 with its wireless remote control, the device 10, the implanted energy-transforming device 3020, an implanted internal control unit 3150 controlled by the wireless remote control of the external energy-transmission device 3040, an implanted accumulator 3160 and an implanted capacitor 3170. The internal control unit 1015 arranges storage of electric energy received from the implanted energy-transforming device 3020 in the accumulator 3160, which supplies energy to the device 10. In response to a control signal from the wireless remote control of the external energy-transmission device 3040, the internal control unit 3150 either releases electric energy from the accumulator 3160 and transfers the released energy via power lines 3180 and 3190, or directly transfers electric energy from the implanted energy-transforming device 3020 via a power line 3200, the capacitor 3170, which stabilizes the electric current, a power line 3210 and the power line 3190, for the operation of the device 10.

The internal control unit is preferably programmable from outside the patient's body. In a preferred embodiment, the internal control unit is programmed to regulate the device 10 according to a pre-programmed time-schedule or to input from any sensor sensing any possible physical parameter of the patient or any functional parameter of the system.

In accordance with an alternative, the capacitor 3170 in the embodiment of FIG. 7 may be omitted. In accordance with another alternative, the accumulator 3160 in this embodiment may be omitted.

Figure 23:
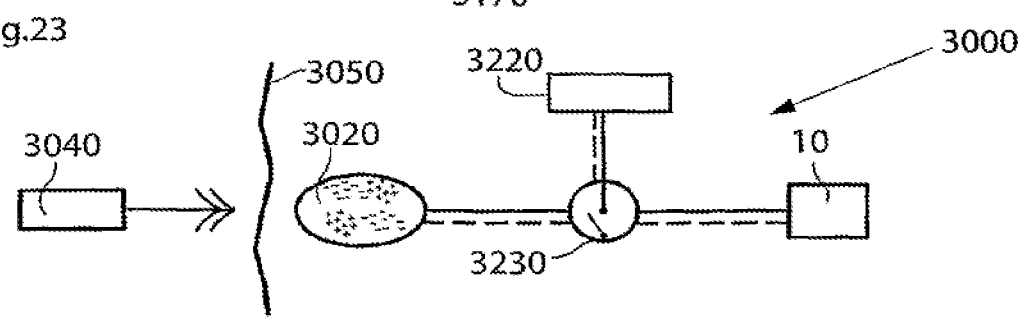

FIG. 23 shows an embodiment of the invention identical to that of FIG. 17, except that a battery 3220 for supplying energy for the operation of the device 10 and an electric switch 3230 for switching the operation of the device 10 also are implanted in the patient. The electric switch 3230 may be controlled by the remote control and may also be operated by the energy supplied by the implanted energy-transforming device 3020 to switch from an off mode, in which the battery 3220 is not in use, to an on mode, in which the battery 3220 supplies energy for the operation of the device 10.

Figure 24:
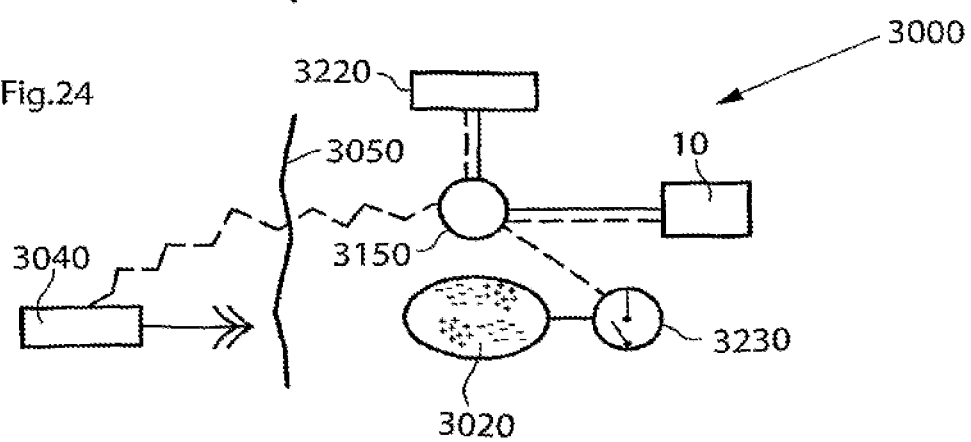

FIG. 24 shows an embodiment of the invention identical to that of FIG. 23, except that an internal control unit 3150 controllable by the wireless remote control of the external energy-transmission device 3040 also is implanted in the patient. In this case, the electric switch 3230 is operated by the energy supplied by the implanted energy-transforming device 3020 to switch from an off mode, in which the wireless remote control is prevented from controlling the internal control unit 3150 and the battery is not in use, to a standby mode, in which the remote control is permitted to control the internal control unit 3150 to release electric energy from the battery 3220 for the operation of the device 10.

Figure 25:
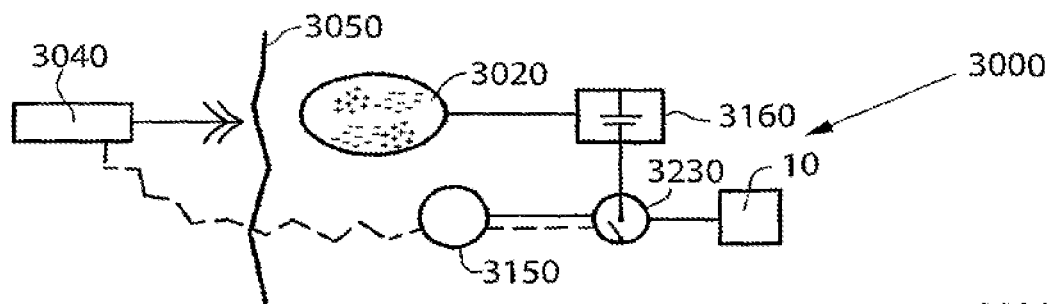

FIG. 25 shows an embodiment of the invention identical to that of FIG. 24, except that an accumulator 3160 is substituted for the battery 3220 and the implanted components are interconnected differently. In this case, the accumulator 3160 stores energy from the implanted energy-transforming device 3020. In response to a control signal from the wireless remote control of the external energy-transmission device 3040, the internal control unit 3150 controls the electric switch 3230 to switch from an off mode, in which the accumulator 3160 is not in use, to an on mode, in which the accumulator 3160 supplies energy for the operation of the device 10. The accumulator may be combined with or replaced by a capacitor.

Figure 26:
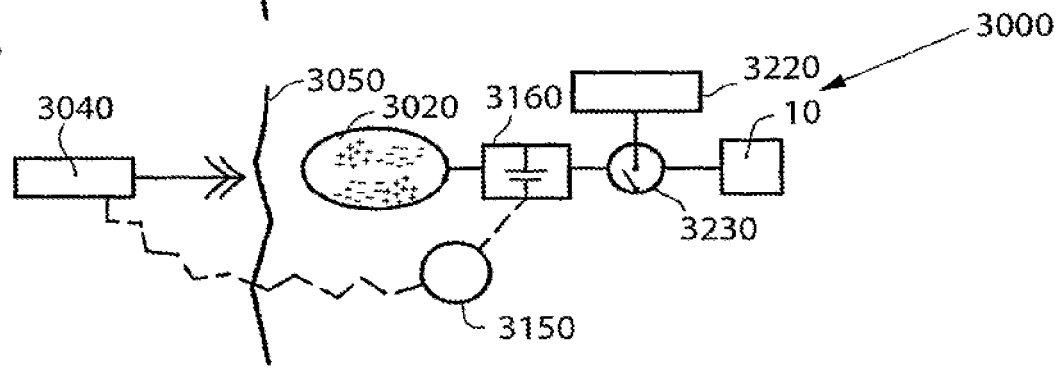

FIG. 26 shows an embodiment of the invention identical to that of FIG. 25, except that a battery 3220 also is implanted in the patient and the implanted components are interconnected differently. In response to a control signal from the wireless remote control of the external energy-transmission device 3040, the internal control unit 3150 controls the accumulator 3160 to deliver energy for operating the electric switch 3230 to switch from an off mode, in which the battery 3220 is not in use, to an on mode, in which the battery 3220 supplies electric energy for the operation of the device 10.

Alternatively, the electric switch 3230 may be operated by energy supplied by the accumulator 3160 to switch from an off mode, in which the wireless remote control is prevented from controlling the battery 3220 to supply electric energy and is not in use, to a standby mode, in which the wireless remote control is permitted to control the battery 3220 to supply electric energy for the operation of the device 10.

It should be understood that the switch 3230 and all other switches in this application should be interpreted in its broadest embodiment. This means a transistor, MCU, MCPU, ASIC, FPGA or a DA converter or any other electronic component or circuit that may switch the power on and off. Preferably the switch is controlled from outside the body, or alternatively by an implanted internal control unit.

Figure 27:
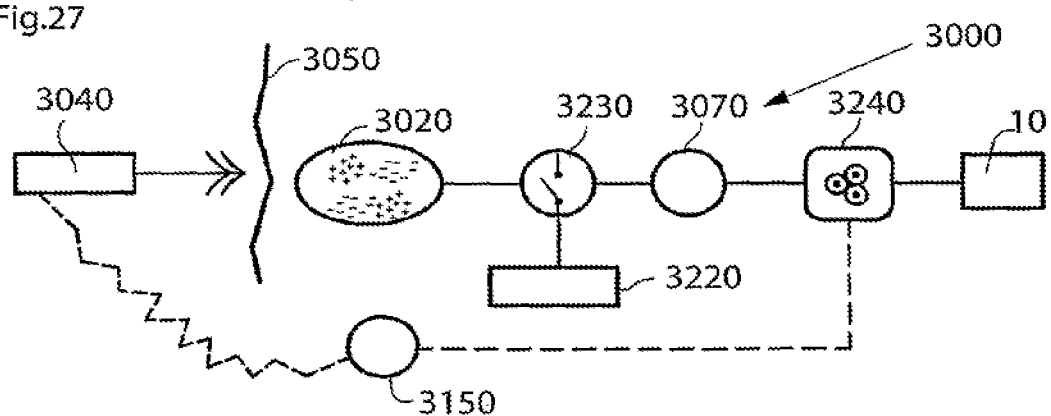

FIG. 27 shows an embodiment of the invention identical to that of FIG. 23, except that a motor 3070, a mechanical reversing device in the form of a gear box 3240, and an internal control unit 3150 for controlling the gear box 3240 also are implanted in the patient. The internal control, unit 3150 controls the gear box 3240 to reverse the function performed by the device 10 (mechanically operated). Even simpler is to switch the direction of the motor electronically. The gear box interpreted in its broadest embodiment may stand for a servo arrangement saving force for the operation device in favor of longer stroke to act.

Figure 28:
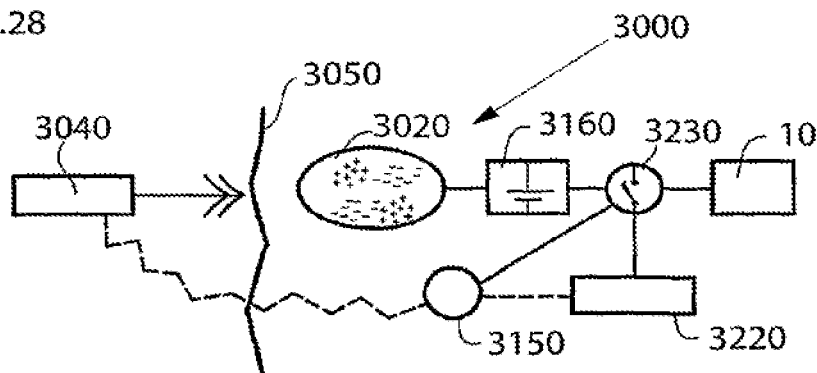

FIG. 28 shows an embodiment of the invention identical to that of FIG. 24 except that the implanted components are interconnected differently. Thus, in this case the internal control unit 3150 is powered by the battery 3220 when the accumulator 3160, suitably a capacitor, activates the electric switch 3230 to switch to an on mode. When the electric switch 3230 is in its on mode the internal control unit 3150 is permitted to control the battery 3220 to supply, or not supply, energy for the operation of the device 10.

Figure 29:
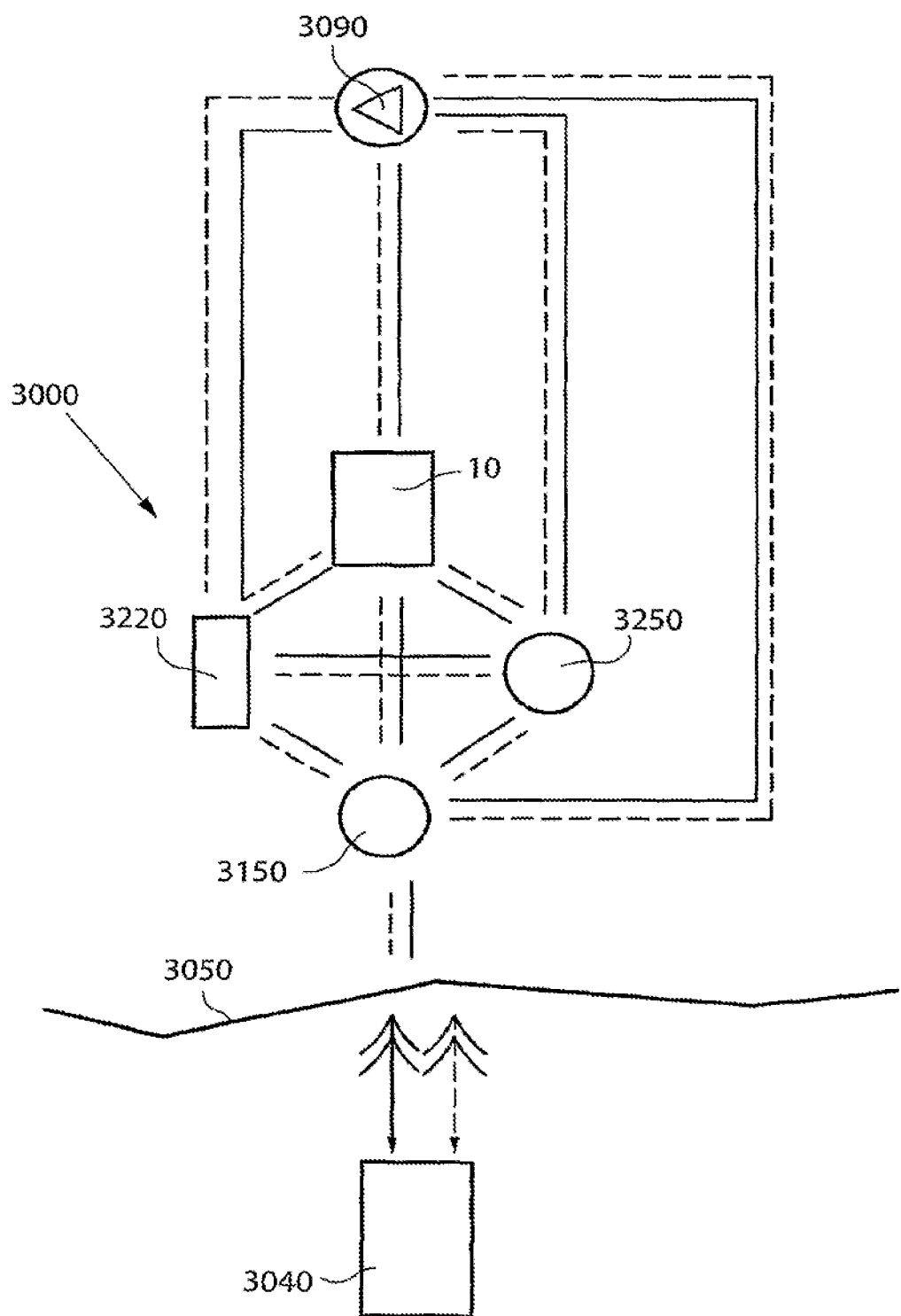

FIG. 29 schematically shows conceivable combinations of implanted components of the device for achieving various communication options. Basically, there are the device 10, the internal control unit 3150, motor or pump unit 3090, and the external energy-transmission device 3040 including the external wireless remote control. As already described above the wireless remote control transmits a control signal which is received by the internal control unit 3150, which in turn controls the various implanted components of the device.

A feedback device, preferably comprising a sensor or measuring device 3250, may be implanted in the patient for sensing a physical parameter of the patient. The physical parameter may be at least one selected from the group consisting of: pressure, volume, diameter, stretching, elongation, extension, movement, bending, elasticity, muscle, contraction, nerve impulse, body temperature, blood pressure, blood flow, heartbeats and breathing. The sensor may sense any of the above physical parameters. For example, the sensor may be a pressure or motility sensor. Alternatively, the sensor 3250 may be arranged to sense a functional parameter. The functional parameter may be correlated to the transfer of energy for charging an implanted energy source and may further include at least one selected from the group of parameters consisting of; electricity, any electrical parameter, pressure, volume, diameter, stretch, elongation, extension, movement, bending, elasticity, temperature and flow.

The feedback may be sent to the internal control unit or out to an external control unit preferably via the internal control unit. Feedback may be sent out from the body via the energy transfer system or a separate communication system with receiver and transmitters.

The internal control unit 3150, or alternatively the external wireless remote control of the external energy-transmission device 3040, may control the device 10 in response to signals from the sensor 3250. A transceiver may be combined with the sensor 3250 for sending information on the sensed physical parameter to the external wireless remote control. The wireless remote control may comprise a signal transmitter or transceiver and the internal control unit 3150 may comprise a signal receiver or transceiver. Alternatively, the wireless remote control may comprise a signal receiver or transceiver and the internal control unit 3150 may comprise a signal transmitter or transceiver. The above transceivers, transmitters and receivers may be used for sending information or data related to the device 10 from inside the patient's body to the outside thereof.

Where the motor/pump unit 3090 and battery 3220 for powering the motor/pump unit 3090 are implanted, information related to the charging of the battery 3220 may be fed back. To be more precise, when charging a battery or accumulator with energy feed back information related to said charging process is sent and the energy supply is changed accordingly.

Figure 30:
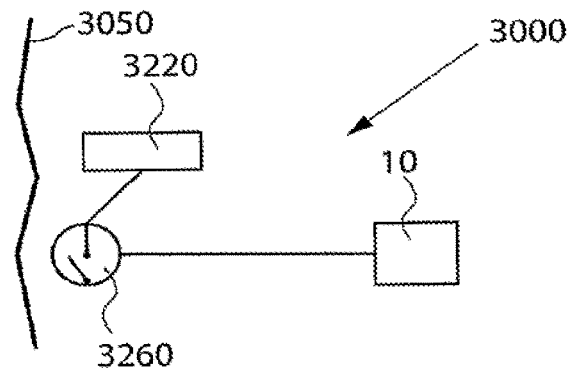

FIG. 30 shows an alternative embodiment wherein the device 10 is regulated from outside the patient's body. The system 3000 comprises a battery 3220 connected to the device 10 via a subcutaneous electric switch 3260. Thus, the regulation of the device 10 is performed non-invasively by manually pressing the subcutaneous switch, whereby the operation of the device 10 is switched on and off. It will be appreciated that the shown embodiment is a simplification and that additional components, such as an internal control unit or any other part disclosed in the present application can be added to the system. Two subcutaneous switches may also be used. In the preferred embodiment one implanted switch sends information to the internal control unit to perform a certain predetermined performance and when the patient press the switch again the performance is reversed.

Figure 31:
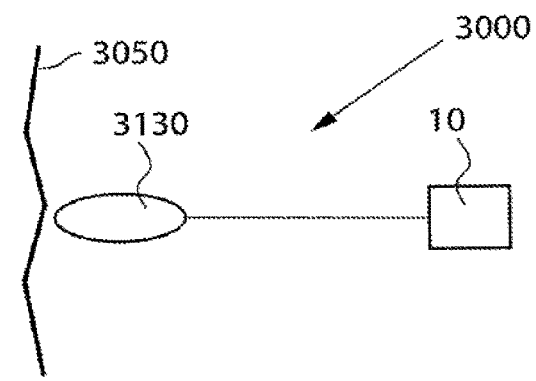

FIG. 31 shows an alternative embodiment, wherein the system 3000 comprises a hydraulic fluid reservoir 3130 hydraulically connected to the device. Non-invasive regulation is performed by manually pressing the hydraulic reservoir connected to the device.

The system may include an external data communicator and an implantable internal data communicator communicating with the external data communicator. The internal communicator feeds data related to the device or the patient to the external data communicator and/or the external data communicator feeds data to the internal data communicator.

Figure 32:
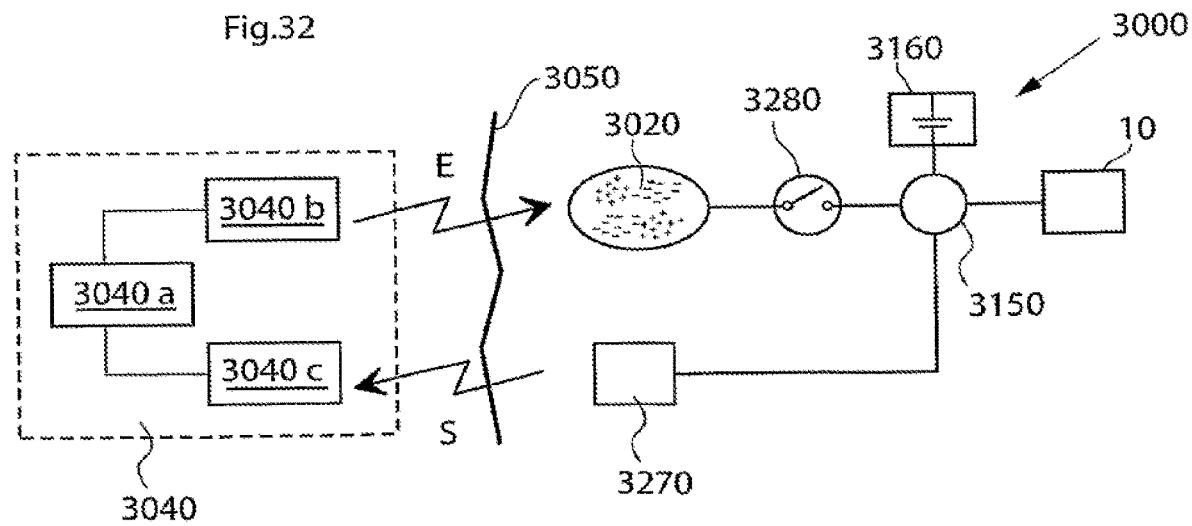
FIG. 32 is a schematic block diagram illustrating an arrangement for supplying an acute amount of energy used for the operation of the device shown in FIG. 16.

FIG. 32 schematically illustrates an arrangement of the system that is capable of sending information from inside the patient's body to the outside thereof to give feedback information related to at least one functional parameter of the device or system, or related to a physical parameter of the patient, in order to supply an accurate amount of energy to an implanted internal energy receiver 3020 connected to implanted energy consuming components of the device 10. Such an energy receiver 3020 may include an energy source and/or an energy-transforming device. Briefly described, wireless energy is transmitted from an external energy source 3040a located outside the patient and is received by the internal energy receiver 3020 located inside the patient. The internal energy receiver is adapted to directly or indirectly supply received energy to the energy consuming components of the device 10 via a switch 3260. An energy balance is determined between the energy received by the internal energy receiver 3020 and the energy used for the device 10, and the transmission of wireless energy is then controlled based on the determined energy balance. The energy balance thus provides an accurate indication of the correct amount of energy needed, which is sufficient to operate the device 10 properly, but without causing undue temperature rise.

In FIG. 32 the patient's skin is indicated a vertical line 3050. Here, the energy receiver comprises an energy-transforming device 1002 located inside the patient, preferably just beneath the patient's skin 3050. Generally speaking, the implanted energy-transforming device 1002 may be placed in the abdomen, thorax, muscle fascia (e.g. in the abdominal wall), subcutaneously, or at any other suitable location. The implanted energy-transforming device 3020 is adapted to receive wireless energy E transmitted from the external energy-source 3040a provided in an external energy-transmission device 3040 located outside the patient's skin 3050 in the vicinity of the implanted energy-transforming device 3020.

As is well known in the art, the wireless energy E may generally be transferred by means of any suitable Transcutaneous Energy Transfer (TET) device, such as a device including a primary coil arranged in the external energy source 1004a and an adjacent secondary coil arranged in the implanted energy-transforming device 3020. When an electric current is fed through the primary coil, energy in the form of a voltage is induced in the secondary coil which can be used to power the implanted energy consuming components of the device, e.g. after storing the incoming energy in an implanted energy source, such as a rechargeable battery or a capacitor. However, the present invention is generally not limited a any particular energy transfer technique, TET devices or energy sources, and any kind of wireless energy may be used.

The amount of energy received by the implanted energy receiver may be compared with the energy used by the implanted components of the device. The term "energy used" is then understood to include also energy stored by implanted components of the device. A control device includes an external control unit 3040b that controls the external energy source 3040a based on the determined energy balance to regulate the amount of transferred energy. In order to transfer the correct amount of energy, the energy balance and the required amount of energy is determined by means of a determination device including an implanted internal control unit 3150 connected between the switch 3260 and the device 10. The internal control unit 3150 may thus be arranged to receive various measurements obtained by suitable sensors or the like, not shown, measuring certain characteristics of the device 10, somehow reflecting the required amount of energy needed for proper operation of the device 10. Moreover, the current condition of the patient may also be detected by means of suitable measuring devices or sensors, in order to provide parameters reflecting the patient's condition. Hence, such characteristics and/or parameters may be related to the current state of the device 10, such as power consumption, operational mode and temperature, as well as the patient's condition reflected by parameters such as; body temperature, blood pressure, heartbeats and breathing. Other kinds of physical parameters of the patient and functional parameters of the device are described elsewhere.

Furthermore, an energy source in the form of an accumulator 3160 may optionally be connected to the implanted energy-transforming device 3020 via the control unit 3150 for accumulating received energy for later use by the device 10. Alternatively or additionally, characteristics of such an accumulator, also reflecting the required amount of energy, may be measured as well. The accumulator may be replaced by a rechargeable battery, and the measured characteristics may be related to the current state of the battery, any electrical parameter such as energy consumption voltage, temperature, etc. In order to provide sufficient voltage and current to the device 10, and also to avoid excessive heating, it is clearly understood that the battery should be charged optimally by receiving a correct amount of energy from the implanted energy-transforming device 3020, i.e. not too little or too much. The accumulator may also be a capacitor with corresponding characteristics.

For example, battery characteristics may be measured on a regular basis to determine the current state of the battery, which then may be stored as state information in a suitable storage means in the internal control unit 3150. Thus, whenever new measurements are made, the stored battery state information can be updated accordingly. In this way, the state of the battery can be "calibrated" by transferring a correct amount of energy, so as to maintain the battery in an optimal condition.

Thus, the internal control unit 3150 of the determination device is adapted to determine the energy balance and/or the currently required amount of energy, (either energy per time unit or accumulated energy) based on measurements made by the above-mentioned sensors or measuring devices of the device 10, or the patient, or an implanted energy source if used, or any combination thereof. The internal control unit 3150 is further connected to an internal signal transmitter 3270, arranged to transmit a control signal reflecting the determined required amount of energy, to an external signal receiver 3040c connected to the external control unit 3040b. The amount of energy transmitted from the external energy source 3040a may then be regulated in response to the received control signal.

Alternatively, the determination device may include the external control unit 3040b. In this alternative, sensor measurements can be transmitted directly to the external control unit 3040b wherein the energy balance and/or the currently required amount of energy can be determined by the external control unit 3040b, thus integrating the above-described function of the internal control unit 3150 in the external control unit 3040b. In that case, the internal control unit 3150 can be omitted and the sensor measurements are supplied directly to the internal signal transmitter 3270 which sends the measurements over to the external signal receiver 3040c and the external control unit 3040b. The energy balance and the currently required amount of energy can then be determined by the external control unit 3040b based on those sensor measurements.

Hence, the present solution according to the arrangement of FIG. 32 employs the feed back of information indicating the required energy, which is more efficient than previous solutions because it is based on the actual use of energy that is compared to the received energy, e.g. with respect to the amount of energy, the energy difference, or the energy receiving rate as compared to the energy rate used by implanted energy consuming components of the device. The device may use the received energy either for consuming or for storing the energy in an implanted energy source or the like. The different parameters discussed above would thus be used if relevant and needed and then as a tool for determining the actual energy balance. However, such parameters may also be needed per se for any actions taken internally to specifically operate the device.

The internal signal transmitter 3270 and the external signal receiver 3040c may be implemented as separate units using suitable signal transfer means, such as radio, IR (Infrared) or ultrasonic signals. Alternatively, the internal signal transmitter 3270 and the external signal receiver 3040c may be integrated in the implanted energy-transforming device 3020 and the external energy source 3040a, respectively, so as to convey control signals in a reverse direction relative to the energy transfer, basically using the same transmission technique. The control signals may be modulated with respect to frequency, phase or amplitude.

Thus, the feedback information may be transferred either by a separate communication system including receivers and transmitters or may be integrated in the energy system. In accordance with the present invention, such an integrated information feedback and energy system comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil. The external second coil of the energy transmitter transmits wireless energy which is received by the first coil of the energy receiver. This system further comprises a power switch for switching the connection of the internal first coil to the first electronic circuit on and off, such that feedback information related to the charging of the first coil is received by the external energy transmitter in the form of an impedance variation in the load of the external second coil, when the power switch switches the connection of the internal first coil to the first electronic circuit on and off. In implementing this system in the arrangement of FIG. 32, the switch 3260 is either separate and controlled by the internal control unit 3150, or integrated in the internal control unit 3150. It should be understood that the switch 3260 should be interpreted in its broadest embodiment. This means a transistor, MCU, MCPU, ASIC FPGA or a DA converter or any other electronic component or circuit that may switch the power on and off.

To conclude, the energy supply arrangement illustrated in FIG. 32 may operate basically in the following manner. The energy balance is first determined by the internal control unit 3150 of the determination device. A control signal reflecting the required amount of energy is also created by the internal control unit 3150, and the control signal is transmitted from the internal signal transmitter 3270 to the external signal receiver 3040c. Alternatively, the energy balance can be determined by the external control unit 3040b instead depending on the implementation, as mentioned above. In that case, the control signal may carry measurement results from various sensors. The amount of energy emitted from the external energy source 1004a can then be regulated by the external control unit 3040b, based on the determined energy balance, e.g. in response to the received control signal. This process may be repeated intermittently at certain intervals during ongoing energy transfer, or may be executed on a more or less continuous basis during the energy transfer.

The amount of transferred energy can generally be regulated by adjusting various transmission parameters in the external energy source 3040a, such as voltage, current, amplitude, wave frequency and pulse characteristics.

This system may also be used to obtain information about the coupling factors between the coils in a TET system even to calibrate the system both to find an optimal place for the external coil in relation to the internal coil and to optimize energy transfer. Simply comparing in this case the amount of energy transferred with the amount of energy received. For example if the external coil is moved the coupling factor may vary and correctly displayed movements could cause the external coil to find the optimal place for energy transfer. Preferably, the external coil is adapted to calibrate the amount of transferred energy to achieve the feedback information in the determination device, before the coupling factor is maximized.

This coupling factor information may also be used as a feedback during energy transfer. In such a case, the energy system of the present invention comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil. The external second coil of the energy transmitter transmits wireless energy which is received by the first coil of the energy receiver. This system further comprises a feedback device for communicating out the amount of energy received in the first coil as a feedback information, and wherein the second electronic circuit includes a determination device for receiving the feedback information and for comparing the amount of transferred energy by the second coil with the feedback information related to the amount of energy received in the first coil to obtain the coupling factor between the first and second coils. The energy transmitter may regulate the transmitted energy in response to the obtained coupling factor.

Figure 33:
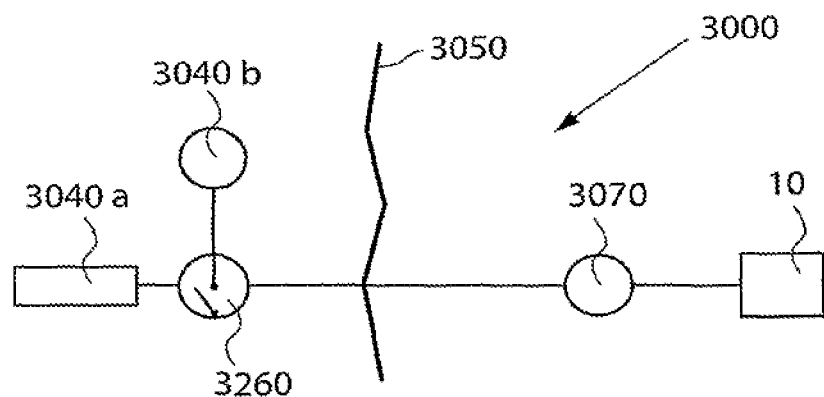
FIG. 33 schematically shows an embodiment of the system, in which the device is operated with wire bound energy.

With reference to FIG. 33, although wireless transfer of energy for operating the device has been described above to enable non-invasive operation, it will be appreciated that the device can be operated with wire bound energy as well. Such an example is shown in FIG. 33, wherein an external switch 3260 is interconnected between the external energy source 3040a and an operation device, such as an electric motor 3070 operating the device 10. An external control unit 3040b controls the operation of the external switch 3260 to effect proper operation of the device 10.

Figure 34:
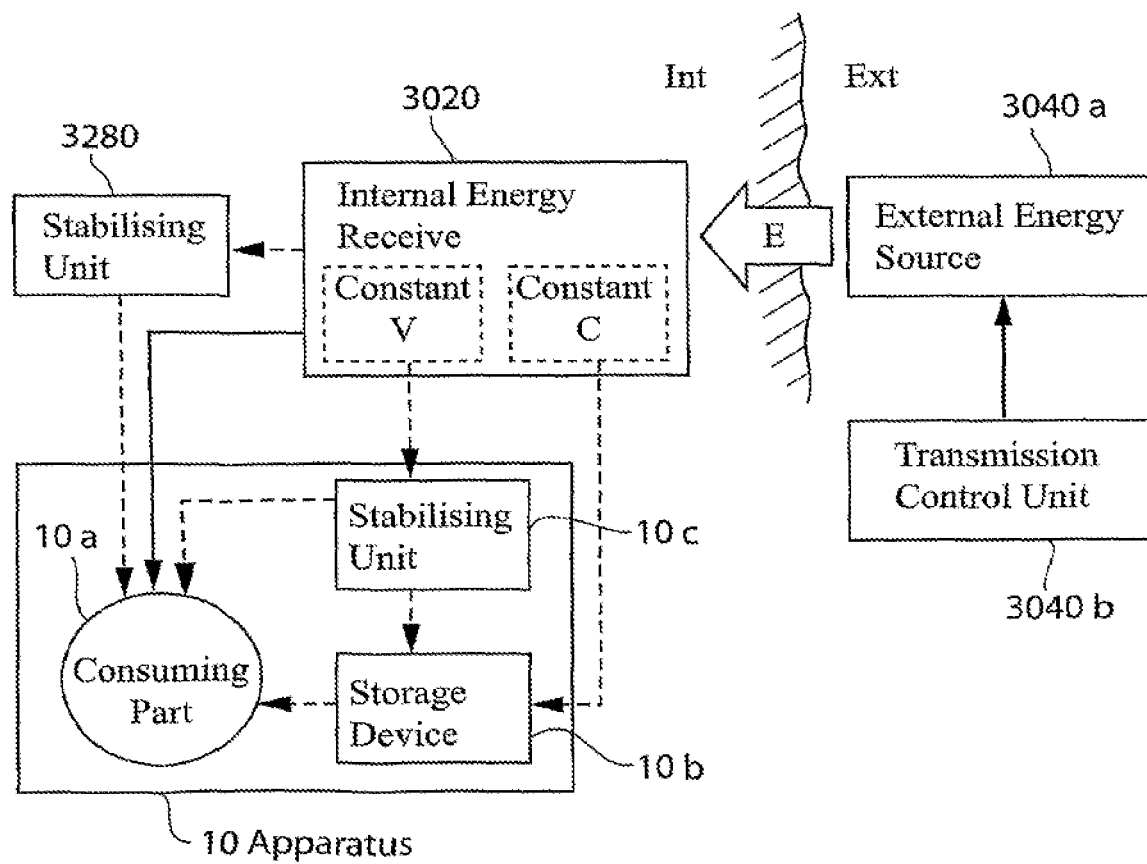
FIG. 34 is a more detailed block diagram of an arrangement for controlling the transmission of wireless energy used for the operation of the device shown in FIG. 16.

FIG. 34 illustrates different embodiments for how received energy can be supplied to and used by the device 10. Similar to the example of FIG. 32, an internal energy receiver 3020 receives wireless energy E from an external energy source 3040a which is controlled by a transmission control unit 3040b. The internal energy receiver 3020 may comprise a constant voltage circuit, indicated as a dashed box "constant V" in the figure, for supplying energy at constant voltage to the device 10. The internal energy receiver 3020 may further comprise a constant current circuit, indicated as a dashed box "constant C" in the figure, for supplying energy at constant current to the device 10.

The device 10 comprises an energy consuming part 10a, which may be a motor, pump, restriction device, or any other medical appliance that requires energy for its electrical operation. The device 10 may further comprise an energy storage device 10b for storing energy supplied from the internal energy receiver 3020. Thus, the supplied energy may be directly consumed by the energy consuming part 10a, or stored by the energy storage device 10b, or the supplied energy may be partly consumed and partly stored. The device 10 may further comprise an energy stabilizing unit 10c for stabilizing the energy supplied from the internal energy receiver 3020. Thus, the energy may be supplied in a fluctuating manner such that it may be necessary to stabilize the energy before consumed or stored.

The energy supplied from the internal energy receiver 3020 may further be accumulated and/or stabilized by a separate energy stabilizing unit 3280 located outside the device 10, before being consumed and/or stored by the device 10. Alternatively, the energy stabilizing unit 3280 may be integrated in the internal energy receiver 3020. In either case, the energy stabilizing unit 3280 may comprise a constant voltage circuit and/or a constant current circuit.

It should be noted that FIG. 32 and FIG. 34 illustrate some possible but non-limiting implementation options regarding how the various shown functional components and elements can be arranged and connected to each other. However, the skilled person will readily appreciate that many variations and modifications can be made within the scope of the present invention.

Figure 35:
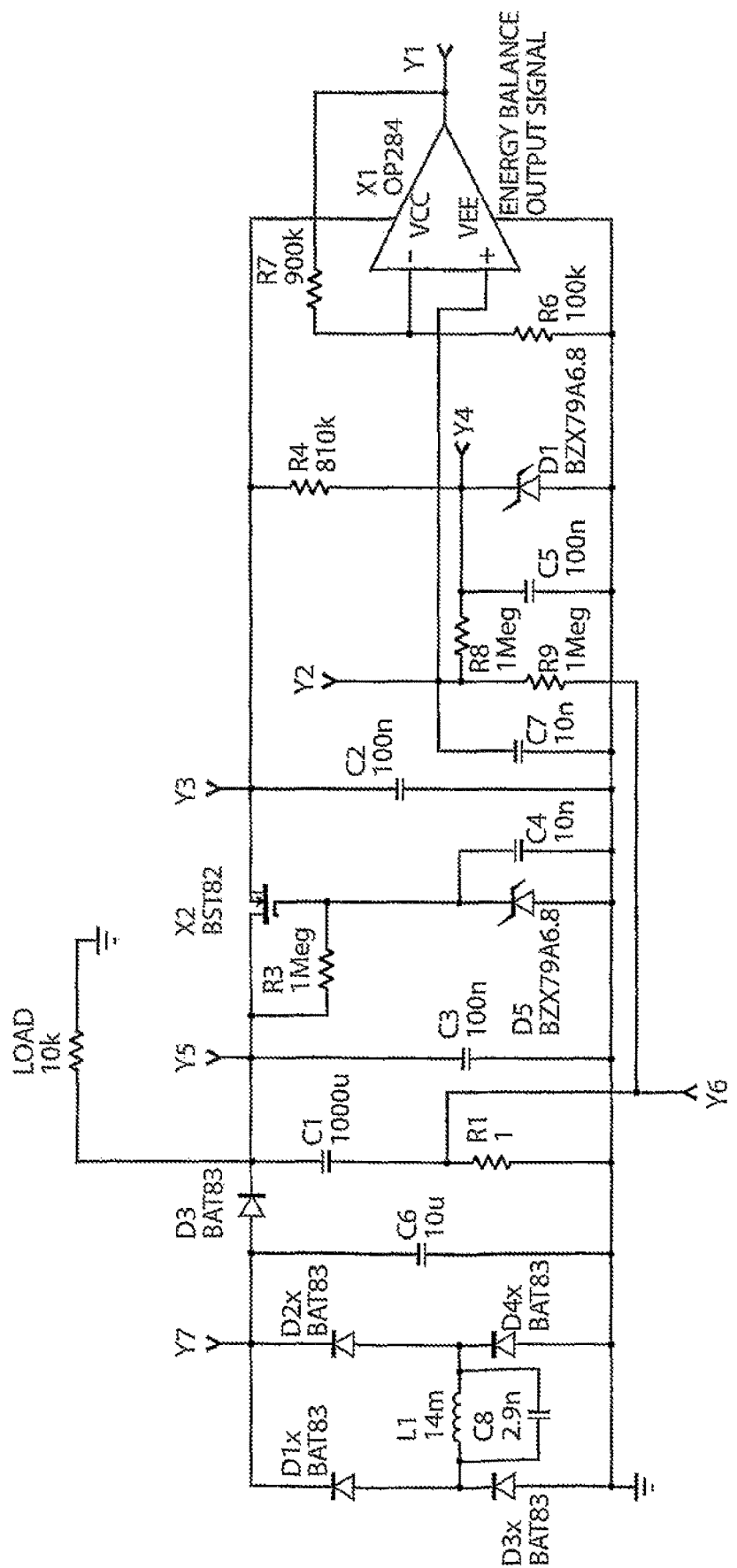
FIG. 35 is a circuit for the arrangement shown in FIG. 34, according to a possible implementation example.

FIG. 35 schematically shows an energy balance measuring circuit of one of the proposed designs of the system for controlling transmission of wireless energy, or energy balance control system. The circuit has an output signal centered on 2.5V and proportionally related to the energy imbalance. The derivative of this signal shows if the value goes up and down and how fast such a change takes place. If the amount of received energy is lower than the energy used by implanted components of the device, more energy is transferred and thus charged into the energy source. The output signal from the circuit is typically feed to an A/D converter and converted into a digital format. The digital information can then be sent to the external energy-transmission device allowing it to adjust the level of the transmitted energy. Another possibility is to have a completely analog system that uses comparators comparing the energy balance level with certain maximum and minimum thresholds sending information to external energy-transmission device if the balance drifts out of the max/min window.

The schematic FIG. 35 shows a circuit implementation for a system that transfers energy to the implanted energy components of the device of the present invention from outside of the patient's body using inductive energy transfer. An inductive energy transfer system typically uses an external transmitting coil and an internal receiving coil. The receiving coil, L1, is included in the schematic FIG. 18; the transmitting parts of the system are excluded.

The implementation of the general concept of energy balance and the way the information is transmitted to the external energy transmitter can of course be implemented in numerous different ways. The schematic FIG. 35 and the above described method of evaluating and transmitting the information should only be regarded as examples of how to implement the control system.

Circuit Details

In FIG. 35 the symbols Y1, Y2, Y3 and so on symbolize test points within the circuit. The components in the diagram and their respective values are values that work in this particular implementation which of course is only one of an infinite number of possible design solutions.

Energy to power the circuit is received by the energy receiving coil L2. Energy to implanted components is transmitted in this particular case at a frequency of 25 kHz. The energy balance output signal is present at test point Y1.

Those skilled in the art will realize that the above various embodiments of the system could be combined in many different ways. For example, the electric switch 3060 of FIG. 18 could be incorporated in any of the embodiments of FIGS. 21-27, the hydraulic valve shifting device 3140 of FIG. 21 could be incorporated in the embodiment of FIG. 20, and the gear box 3240 could be incorporated in the embodiment of FIG. 19. Please observe that the switch simply could mean any electronic circuit or component.

The embodiments described in connection with FIGS. 32, 34 and 35 identify a method and a system for controlling transmission of wireless energy to implanted energy consuming components of an electrically operable device. Such a method and system will be defined in general terms in the following.

A method is thus provided for controlling transmission of wireless energy supplied to implanted energy consuming components of a device as described above. The wireless energy E is transmitted from an external energy source located outside the patient and is received by an internal energy receiver located inside the patient, the internal energy receiver being connected to the implanted energy consuming components of the device for directly or indirectly supplying received energy thereto. An energy balance is determined between the energy received by the internal energy receiver and the energy used for the device. The transmission of wireless energy E from the external energy source is then controlled based on the determined energy balance.

The wireless energy may be transmitted inductively from a primary coil in the external energy source to a secondary coil in the internal energy receiver. A change in the energy balance may be detected to control the transmission of wireless energy based on the detected energy balance change. A difference may also be detected between energy received by the internal energy receiver and energy used for the medical device, to control the transmission of wireless energy based on the detected energy difference.

When controlling the energy transmission, the amount of transmitted wireless energy may be decreased if the detected energy balance change implies that the energy balance is increasing, or vice versa. The decrease/increase of energy transmission may further correspond to a detected change rate.

The amount of transmitted wireless energy may further be decreased if the detected energy difference implies that the received energy is greater than the used energy, or vice versa. The decrease/increase of energy transmission may then correspond to the magnitude of the detected energy difference.

As mentioned above, the energy used for the medical device may be consumed to operate the medical device, and/or stored in at least one energy storage device of the medical device.

When electrical and/or physical parameters of the medical device and/or physical parameters of the patient are determined, the energy may be transmitted for consumption and storage according to a transmission rate per time unit which is determined based on said parameters. The total amount of transmitted energy may also be determined based on said parameters.

When a difference is detected between the total amount of energy received by the internal energy receiver and the total amount of consumed and/or stored energy, and the detected difference is related to the integral over time of at least one measured electrical parameter related to said energy balance, the integral may be determined for a monitored voltage and/or current related to the energy balance.

When the derivative is determined over time of a measured electrical parameter related to the amount of consumed and/or stored energy, the derivative may be determined for a monitored voltage and/or current related to the energy balance.

The transmission of wireless energy from the external energy source may be controlled by applying to the external energy source electrical pulses from a first electric circuit to transmit the wireless energy, the electrical pulses having leading and trailing edges, varying the lengths of first time intervals between successive leading and trailing edges of the electrical pulses and/or the lengths of second time intervals between successive trailing and leading edges of the electrical pulses, and transmitting wireless energy, the transmitted energy generated from the electrical pulses having a varied power, the varying of the power depending on the lengths of the first and/or second time intervals.

In that case, the frequency of the electrical pulses may be substantially constant when varying the first and/or second time intervals. When applying electrical pulses, the electrical pulses may remain unchanged, except for varying the first and/or second time intervals. The amplitude of the electrical pulses may be substantially constant when varying the first and/or second time intervals. Further, the electrical pulses may be varied by only varying the lengths of first time intervals between successive leading and trailing edges of the electrical pulses.

A train of two or more electrical pulses may be supplied in a row, wherein when applying the train of pulses, the train having a first electrical pulse at the start of the pulse train and having a second electrical pulse at the end of the pulse train, two or more pulse trains may be supplied in a row, wherein the lengths of the second time intervals between successive trailing edge of the second electrical pulse in a first pulse train and leading edge of the first electrical pulse of a second pulse train are varied.

When applying the electrical pulses, the electrical pulses may have a substantially constant current and a substantially constant voltage. The electrical pulses may also have a substantially constant current and a substantially constant voltage. Further, the electrical pulses may also have a substantially constant frequency. The electrical pulses within a pulse train may likewise have a substantially constant frequency.

The circuit formed by the first electric circuit and the external energy source may have a first characteristic time period or first time constant, and when effectively varying the transmitted energy, such frequency time period may be in the range of the first characteristic time period or time constant or shorter.

A system comprising a device as described above is thus also provided for controlling transmission of wireless energy supplied to implanted energy consuming components of the device. In its broadest sense, the system comprises a control device for controlling the transmission of wireless energy from an energy-transmission device, and an implantable internal energy receiver for receiving the transmitted wireless energy, the internal energy receiver being connected to implantable energy consuming components of the device for directly or indirectly supplying received energy thereto. The system further comprises a determination device adapted to determine an energy balance between the energy received by the internal energy receiver and the energy used for the implantable energy consuming components of the device, wherein the control device controls the transmission of wireless energy from the external energy-transmission device, based on the energy balance determined by the determination device.

Further, the system may comprise any of the following:

A primary coil in the external energy source adapted to transmit the wireless energy inductively to a secondary coil in the internal energy receiver.

The determination device is adapted to detect a change in the energy balance, and the control device controls the transmission of wireless energy based on the detected energy balance change The determination device is adapted to detect a difference between energy received by the internal energy receiver and energy used for the implantable energy consuming components of the device, and the control device controls the transmission of wireless energy based on the detected energy difference.

The control device controls the external energy-transmission device to decrease the amount of transmitted wireless energy if the detected energy balance change implies that the energy balance is increasing, or vice versa, wherein the decrease/increase of energy transmission corresponds to a detected change rate.

The control device controls the external energy-transmission device to decrease the amount of transmitted wireless energy if the detected energy difference implies that the received energy is greater than the used energy, or vice versa, wherein the decrease/increase of energy transmission corresponds to the magnitude of said detected energy difference.

The energy used for the device is consumed to operate the device, and/or stored in at least one energy storage device of the device.

Where electrical and/or physical parameters of the device and/or physical parameters of the patient are determined, the energy-transmission device transmits the energy for consumption and storage according to a transmission rate per time unit which is determined by the determination device based on said parameters. The determination device also determines the total amount of transmitted energy based on said parameters.

When a difference is detected between the total amount of energy received by the internal energy receiver and the total amount of consumed and/or stored energy, and the detected difference is related to the integral over time of at least one measured electrical parameter related to the energy balance, the determination device determines the integral for a monitored voltage and/or current related to the energy balance.

When the derivative is determined over time of a measured electrical parameter related to the amount of consumed and/or stored energy, the determination device determines the derivative for a monitored voltage and/or current related to the energy balance.

The energy-transmission device comprises a coil placed externally to the human body, and an electric circuit is provided to power the external coil with electrical pulses to transmit the wireless energy. The electrical pulses have leading and trailing edges, and the electric circuit is adapted to vary first time intervals between successive leading and trailing edges and/or second time intervals between successive trailing and leading edges of the electrical pulses to vary the power of the transmitted wireless energy. As a result, the energy receiver receiving the transmitted wireless energy has a varied power.

The electric circuit is adapted to deliver the electrical pulses to remain unchanged except varying the first and/or second time intervals.

The electric circuit has a time constant and is adapted to vary the first and second time intervals only in the range of the first time constant, so that when the lengths of the first and/or second time intervals are varied, the transmitted power over the coil is varied.

The electric circuit is adapted to deliver the electrical pulses to be varied by only varying the lengths of first time intervals between successive leading and trailing edges of the electrical pulses.

The electric circuit is adapted to supplying a train of two or more electrical pulses in a row, said train having a first electrical pulse at the start of the pulse train and having a second electrical pulse at the end of the pulse train, and the lengths of the second time intervals between successive trailing edge of the second electrical pulse in a first pulse train and leading edge of the first electrical pulse of a second pulse train are varied by the first electronic circuit.

The electric circuit is adapted to provide the electrical pulses as pulses having a substantially constant height and/or amplitude and/or intensity and/or voltage and/or current and/or frequency.

The electric circuit has a time constant, and is adapted to vary the first and second time intervals only in the range of the first time constant, so that when the lengths of the first and/or second time intervals are varied, the transmitted power over the first coil are varied.

The electric circuit is adapted to provide the electrical pulses varying the lengths of the first and/or the second time intervals only within a range that includes the first time constant or that is located relatively close to the first time constant, compared to the magnitude of the first time constant.

FIGS. 36-39 show in more detail block diagrams of four different ways of hydraulically or pneumatically powering an implanted device according to the invention.

Figure 36:
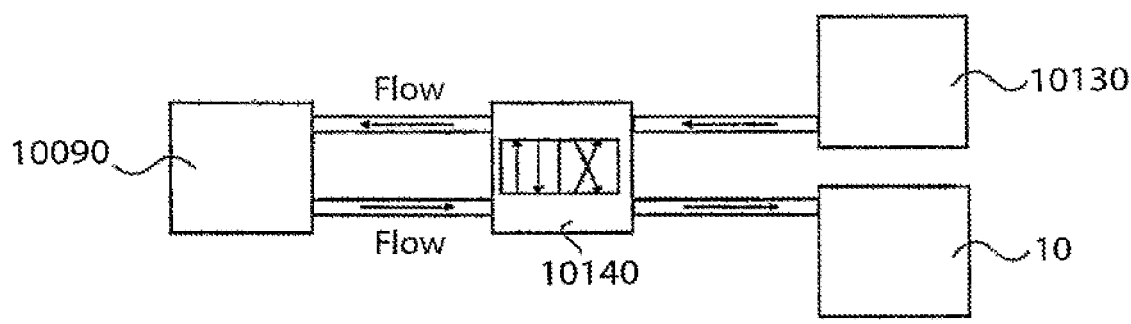
FIGS. 36-42 show various ways of arranging hydraulic or pneumatic powering of a device implanted in a patient.

FIG. 36 shows a system as described above with The system comprises an implanted device 10 and further a separate regulation reservoir 10130, a one way pump 10090 and an alternate valve 10140.

Figure 37:
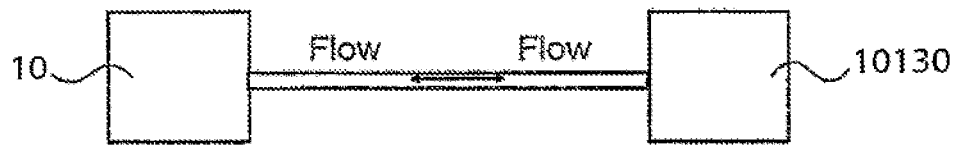

FIG. 37 shows the device 10 and a fluid reservoir 10130. By moving the wall of the regulation reservoir or changing the size of the same in any other different way, the adjustment of the device may be performed without any valve, just free passage of fluid any time by moving the reservoir wall.

Figure 38:
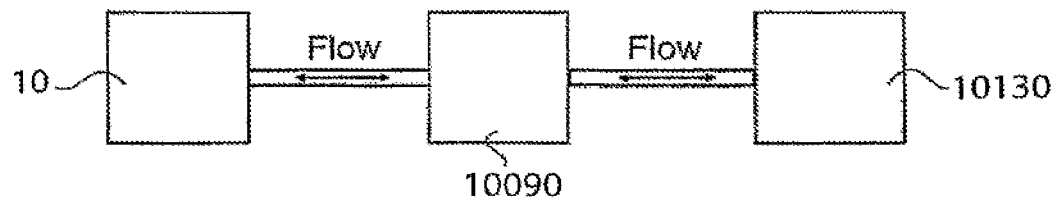

FIG. 38 shows the device 10, a two way pump 10090 and the regulation reservoir 10130.

Figure 39:
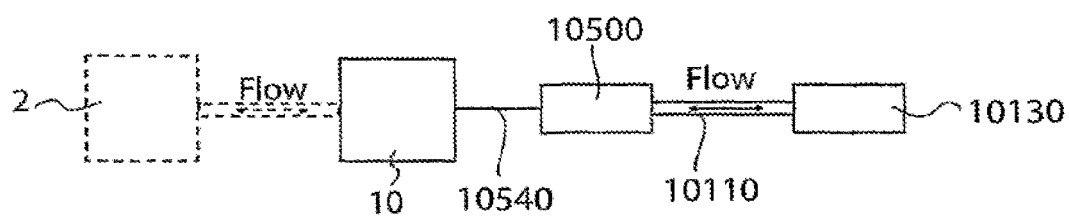

FIG. 39 shows a block diagram of a reversed servo system with a first closed system controlling a second closed system. The servo system comprises a regulation reservoir 10130 and a servo reservoir 10500. The servo reservoir 10500 mechanically controls an implanted device 10 via a mechanical interconnection 10540. The device has an expandable/contactable cavity. This cavity is preferably expanded or contracted by supplying hydraulic fluid from the larger adjustable reservoir 10520 in fluid connection with the device 10. Alternatively, the cavity contains compressible gas, which can be compressed and expanded under the control of the servo reservoir 10500.

The servo reservoir 10500 can also be part of the device itself.

Figure 40A:
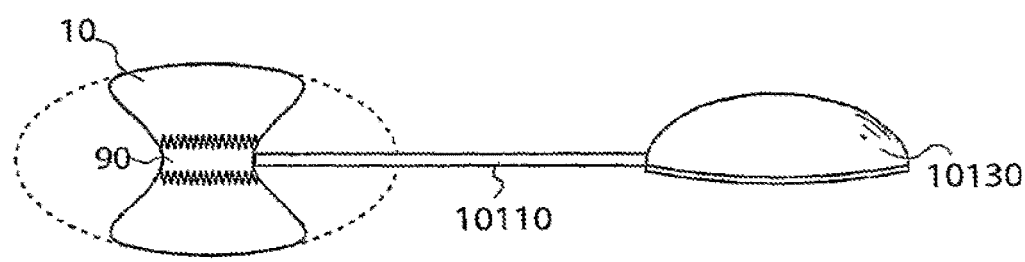
Figure 40B:
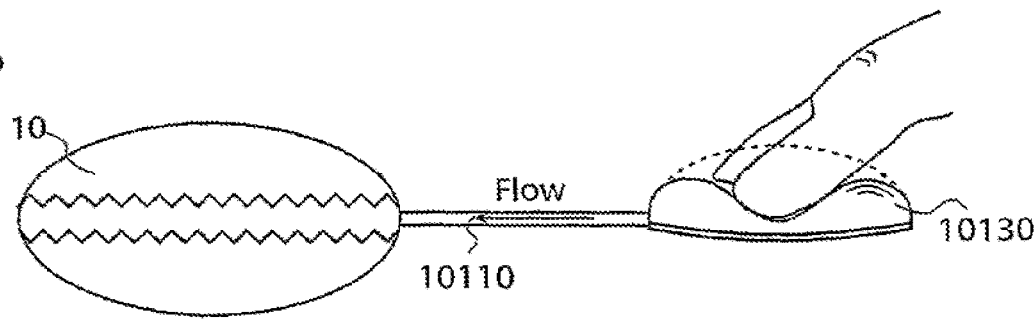
Figure 40C:
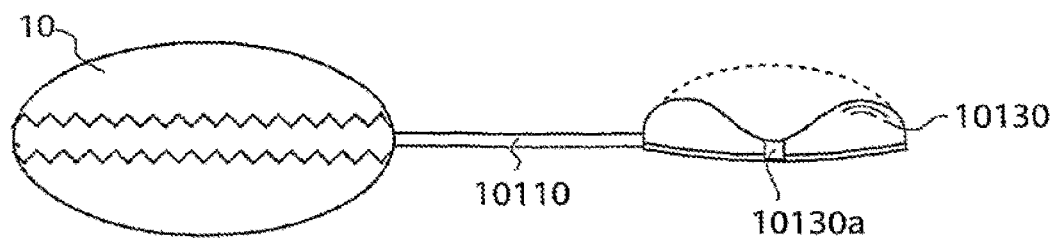
Figure 41:
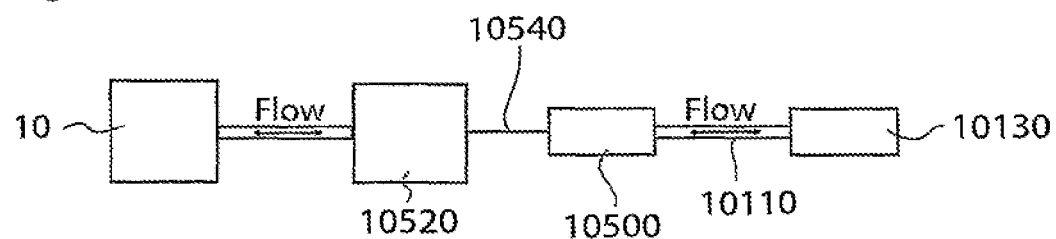

In one embodiment, the regulation reservoir is placed subcutaneous under the patient's skin and is operated by pushing the outer surface thereof by means of a finger. This system is illustrated in FIGS. 40a-c. In FIG. 40a, a flexible subcutaneous regulation reservoir 10130 is shown connected to a bulge shaped servo reservoir 10500 by means of a conduit 10110.

This bellow shaped servo reservoir 10500 is comprised in a flexible device 10. In the state shown in FIG. 40a, the servo reservoir 10500 contains a minimum of fluid and most fluid is found in the regulation reservoir 10130. Due to the mechanical interconnection between the servo reservoir 10500 and the device 10, the outer shape of the device 10 is contracted, i.e., it occupies less than its maximum volume. This maximum volume is shown with dashed lines in the figure.

FIG. 40b shows a state wherein a user, such as the patient in with the device is implanted, presses the regulation reservoir 10130 so that fluid contained therein is brought to flow through the conduit 10110 and into the servo reservoir 10500, which, thanks to its bellow shape, expands longitudinally. This expansion in turn expands the device 10 so that it occupies its maximum volume, thereby stretching the stomach wall, (not shown), which it contacts.

The regulation reservoir 10130 is preferably provided with means 10130a for keeping its shape after compression. This means, which is schematically shown in FIG. 40c, will thus keep the device 10 in a stretched position also when the user releases the regulation reservoir. In this way, the regulation reservoir essentially operates as an on/off switch for the system.

An alternative embodiment of hydraulic or pneumatic operation will now be described with reference to FIGS. 41 and 42a-c. The block diagram shown in FIG. 41 comprises with a first closed system controlling a second closed system. The first system comprises a regulation reservoir 10130 and a servo reservoir 10500. The servo reservoir 10500 mechanically controls a larger adjustable reservoir 10520 via a mechanical interconnection 10540. An implanted device 10 having an expandable/contactable cavity is in turn controlled by the larger adjustable reservoir 10520 by supply of hydraulic fluid from the larger adjustable reservoir 10520 in fluid connection with the device 10.

Figure 42A:
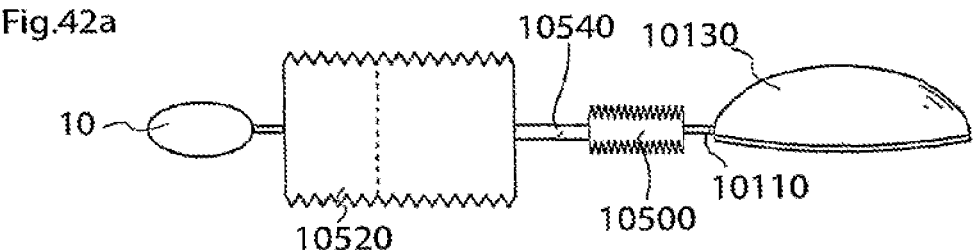
Figure 42B:
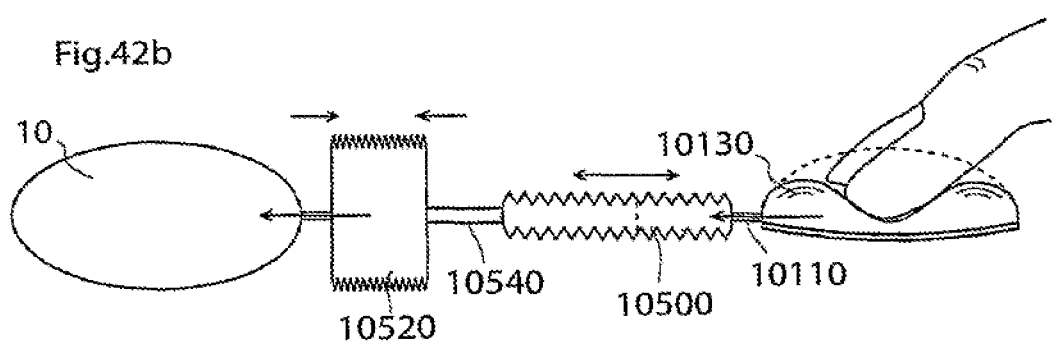
Figure 42C:
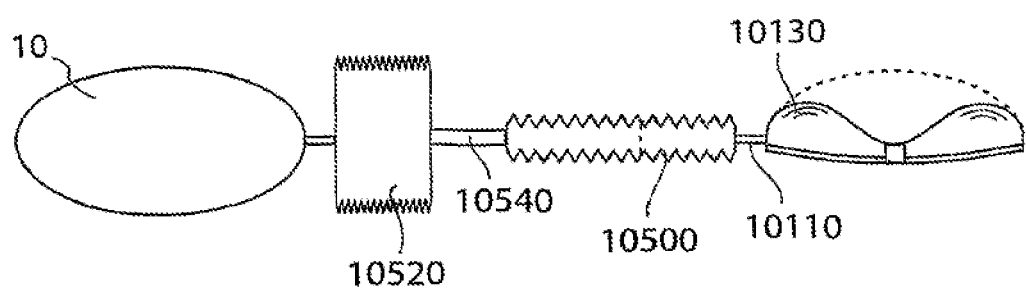

An example of this embodiment will now be described with reference to FIG. 42a-c. Like in the previous embodiment, the regulation reservoir is placed subcutaneous under the patient's skin and is operated by pushing the outer surface thereof by means of a finger. The regulation reservoir 10130 is in fluid connection with a bellow shaped servo reservoir 10500 by means of a conduit 10110. In the first closed system 10130, 10110, 10500 shown in FIG. 42a, the servo reservoir 10500 contains a minimum of fluid and most fluid is found in the regulation reservoir 10130.

The servo reservoir 10500 is mechanically connected to a larger adjustable reservoir 10520, in this example also having a bellow shape but with a larger diameter than the servo reservoir 10500. The larger adjustable reservoir 1052 is in fluid connection with the device 10. This means that when a user pushes the regulation reservoir 10130, thereby displacing fluid from the regulation reservoir 10130 to the servo reservoir 10500, the expansion of the servo reservoir 10500 will displace a larger volume of fluid from the larger adjustable reservoir 10520 to the device 10. In other words, in this reversed servo, a small volume in the regulation reservoir is compressed with a higher force and this creates a movement of a larger total area with less force per area unit.

Like in the previous embodiment described above with reference to FIGS. 40a-c, the regulation reservoir 10130 is preferably provided with means 10130a for keeping its shape after compression. This means, which is schematically shown in the figure, will thus keep the device 10 in a stretched position also when the user releases the regulation reservoir. In this way the regulation reservoir essentially operates as an on/of switch for the system.

The invention claimed is:

1. A device for treating a vascular aneurysm of a human or mammal patient, comprising
an implantable member adapted to hold fluid, the implantable member being adapted to:
be placed against an outside of a blood vessel having the aneurysm,
exercise a pressure on the aneurysm to prevent or reduce an expansion of the aneurysm,
follow an outer contour of the aneurysm, and
wherein the device comprises a control unit and a sensor, wherein the control unit is adapted to control the pressure applied onto the aneurysm such that a pressure is provided being equal or less than the diastolic blood pressure of the human or mammal patient, based on the signal generated by the sensor.

2. The device according to claim 1, wherein the device is adapted to monitor an expansion of the aneurysm.

3. The device according to claim 1, wherein the implantable member is a Y-shaped member, and wherein the implantable Y-shaped member is adapted to be placed at the Aorta Bifurcation.

4. The device according to claim 1, wherein the implantable member is spring loaded.

5. The device according to claim 1, wherein the implantable member is adapted to exert an essentially constant pressure or a pressure reducing the pressure difference, caused by changes in blood pressure in the blood vessel, on the aneurysm.

6. The device according to claim 1, further comprising a control device adapted to increase the pressure on the blood vessel when the aneurysm expands and being implanted in the patient, wherein the control device adapted to increase the pressure on the blood vessel when at least one of:
the aneurysm expands more than a predetermined value, and
the aneurysm expands more than a predetermined value during a time period.

7. The device according to claim 1, further comprising logic circuitry for determining when the aneurysm is expanding based on a signal from a sensor or measuring device.

8. The device according to claim 1, further comprising a sensor or measuring device for sensing or measuring an expansion of the aneurysm, and a volume control unit adapted to directly or indirectly control the volume in the implantable member based on a signal generated by the sensor or measuring device for controlling an expansion of the aneurysm.

9. The device according to claim 8, wherein the volume control unit controls the volume in the implantable member for generating a signal corresponding to a parameter related to the aneurysm or the treatment of the aneurysm based on a signal indicative of at least one of: a parameter that corresponds to the size of the aneurysm, flow of fluid from the implantable member to the first reservoir, volume in the first reservoir, and pressure in the fluid filled implantable member.

10. The device according to claim 1, further comprising a feedback alarm system based on the expansion of the aneurysm being controlled.

11. The device according to claim 1, further comprising an implantable internal energy source for powering implantable energy consuming components of the device.

12. The device according claim 1, further comprising a wireless energy-transmission device for non-invasively energizing implantable energy consuming components of the device.

13. The device according to claim 1, further comprising a feedback device for sending feedback information from inside the patient's body to the outside thereof, the feedback information being related to at least one of a physical parameter of the patient and a functional parameter related to the device.

14. The device according to claim 1, further comprising:
at least one of a sensor or a measuring device, and
an implantable internal control unit, for controlling the device in response to information being related to at least one of:
a physical parameter of the patient sensed by the sensor or measured by the measuring device, or
a functional parameter related to the device sensed by the sensor or measured by the measuring device.

15. The device according to claim 1, further comprising an implantable injection port, adapted to, based on the expansion of the aneurysm being sensed or measured, move a liquid to calibrate the volume in a first reservoir to keep the first reservoir within a pressure regulation volume treatment interval, when the aneurysm expands.

16. The device according to claim 1, wherein the device comprises a hydraulic fluid reservoir and an implantable pump adapted to pump hydraulic fluid from the hydraulic fluid reservoir to the implantable member.

17. The device according to claim 1, wherein the device comprises a hydraulic fluid reservoir adapted to be pressurized for delivering a pressurized hydraulic fluid to the implantable member.

18. The device according to claim 17, wherein the pressurized hydraulic fluid reservoir is spring loaded.

19. The device according to claim 18, wherein the reservoir is adapted to be able to change its volume while keeping substantially the same pressure, such that the same pressure can be kept onto the aneurysm although the aneurysm expands.

* * * * *